US012657730B2

(12) United States Patent
Londono et al.

(10) Patent No.: US 12,657,730 B2
(45) Date of Patent: Jun. 16, 2026

(54) METHODS AND SYSTEMS FOR IMAGE ANNOTATION AND SEGMENTATION

(71) Applicant: GE Precision Healthcare LLC, Wauwatosa, WI (US)

(72) Inventors: Jorge Hernandez Londono, Buc (FR); Vincent Morard, Buc (FR)

(73) Assignee: GE PRECISION HEALTHCARE LLC, Waukesha, WI (US)

( * ) Notice: Subject to any disclaimer, the term of this patent is extended or adjusted under 35 U.S.C. 154(b) by 315 days.

(21) Appl. No.: 18/463,207

(22) Filed: Sep. 7, 2023

(65) Prior Publication Data

US 2025/0086805 A1      Mar. 13, 2025

(51) Int. Cl.
*G06T 7/12* (2017.01)
*G06T 7/174* (2017.01)
(Continued)

(52) U.S. Cl.
CPC ................ *G06T 7/12* (2017.01); *G06T 7/174* (2017.01); *G06T 7/60* (2013.01); *G06V 10/945* (2022.01);
(Continued)

(58) Field of Classification Search
CPC .. G06T 7/12; G06T 7/174; G06T 7/60; G06T 2200/04; G06T 2200/24;
(Continued)

(56) References Cited

U.S. PATENT DOCUMENTS 7,660,463 B2    2/2010  Blake et al.
7,890,890 B2    2/2011  Jarrett et al.
(Continued)

FOREIGN PATENT DOCUMENTS

WO        2021046241 A1      3/2021

OTHER PUBLICATIONS

EP application 24195431.2 filed Aug. 20, 2024—extended Search Report issued Jan. 31, 2025; 11 pages.
(Continued)

*Primary Examiner* — John Villecco
*Assistant Examiner* — Kyla Guan-Ping Tiao Allen
(74) *Attorney, Agent, or Firm* — McCoy Russell LLP

(57)        ABSTRACT
Systems and methods are herein provided for annotation and segmentation of 3D multi-volume imaging data. In one example, a method comprises obtaining three-dimensional (3D) multi-volume imaging data, the 3D multi-volume imaging data comprising a plurality of registered image volumes; determining one or more positions of a user cursor within a first image of a first image volume of the plurality of registered image volumes; determining a contour point position corresponding to each of the one or more positions of the user cursor for two or more of the plurality of registered image volumes; generating two or more segmentation contours corresponding to the two or more of the plurality of registered image volumes; determining, via user input, a selected segmentation contour of the two or more segmentation contours; generating a 3D segmentation mask based at least in part on the selected segmentation contour and saving the 3D segmentation mask to memory.

19 Claims, 15 Drawing Sheets
(1 of 15 Drawing Sheet(s) Filed in Color)

(51) Int. Cl.

| *G06T 7/60* | (2017.01) |
| *G06V 10/94* | (2022.01) |
| *G06V 20/70* | (2022.01) |
| *G16H 30/40* | (2018.01) |

(52) U.S. Cl.
CPC ............. *G06V 20/70* (2022.01); *G16H 30/40* (2018.01); *G06T 2200/04* (2013.01); *G06T 2200/24* (2013.01); *G06T 2207/10024* (2013.01); *G06T 2207/20021* (2013.01); *G06T 2207/20096* (2013.01); *G06T 2207/30101* (2013.01)

(58) Field of Classification Search
CPC . G06T 2207/10024; G06T 2207/20021; G06T 2207/20096; G06T 2207/30101; G06T 2207/10076; G06T 2207/10088; G06T 2207/10104; G06T 2207/10136; G06T 2207/20101; G06T 2207/20108; G06T 2207/20168; G06T 2207/30016; G06T 7/0012; G06V 10/945; G06V 20/70; G06V 10/267; G06V 10/248; G06V 10/44; G16H 30/40; A61B 6/03
See application file for complete search history.

(56) References Cited

U.S. PATENT DOCUMENTS

| 8,175,409 | B1 | 5/2012 | Wilensky |
| 8,923,650 | B2 | 12/2014 | Wexler |
| 9,129,191 | B2 | 9/2015 | Cohen et al. |
| 2001/0033283 | A1 | 10/2001 | Liang et al. |
| 2011/0158491 | A1* | 6/2011 | Markova .................. G06T 7/41 |
| | | | 382/128 |
| 2014/0219534 | A1* | 8/2014 | Wiemker ............... G06T 7/187 |
| | | | 382/131 |
| 2017/0228867 | A1* | 8/2017 | Baruch ..................... G06T 7/12 |
| 2020/0054398 | A1* | 2/2020 | Kovtun .................. G16H 40/63 |
| 2020/0286240 | A1* | 9/2020 | Ouji ...................... G06T 7/0012 |
| 2020/0372658 | A1* | 11/2020 | De Winde ................ G06T 7/11 |
| 2021/0035290 | A1* | 2/2021 | Aben .................... G06T 7/0012 |
| 2021/0110198 | A1* | 4/2021 | Rhodes ................. G06V 10/82 |
| 2022/0138361 | A1* | 5/2022 | Bossard ............. G06F 3/04812 |
| | | | 703/1 |
| 2023/0082049 | A1* | 3/2023 | Moreau ................ G06T 17/205 |
| | | | 345/419 |

OTHER PUBLICATIONS

Faber Matthias et al: "Live-wire-based segmentation using similarities between corresponding image structures" Computerized Medical Imaging and Graphics., vol. 31, No. 7. Oct. 2007 (Oct. 1, 2007), pp. 549-560.
Farber M et al: "Automatic atlas-based contour extracttion of anatomical structures in medical images" International Congress Series; Exceprta Medica Amsterdam, NL, vol. 1281, May 1, 2005 (May 1, 2005), pp. 272-277.
Viergever M A et al: "Integration of functional and anatomical brain images", Biophysical Chemistry; Elsevier; Amsterdam; NL, vol. 68, No. 1-3, Oct. 1, 1997 (Oct. 1, 1997), pp. 207-219, XP008119369.

* cited by examiner

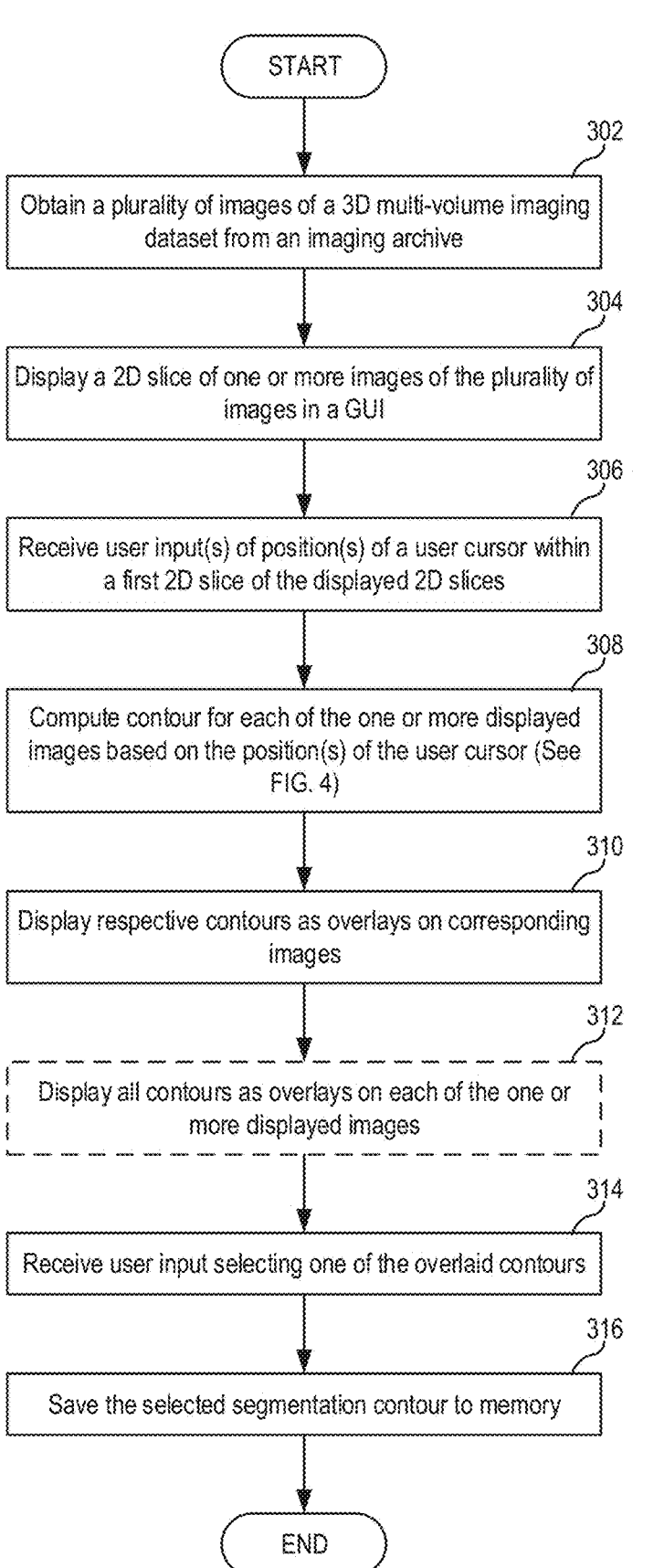

300

START

302
Obtain a plurality of images of a 3D multi-volume imaging dataset from an imaging archive 304
Display a 2D slice of one or more images of the plurality of images in a GUI 306
Receive user input(s) of position(s) of a user cursor within a first 2D slice of the displayed 2D slices 308
Compute contour for each of the one or more displayed images based on the position(s) of the user cursor (See FIG. 4)

310
Display respective contours as overlays on corresponding images

312
Display all contours as overlays on each of the one or more displayed images 314
Receive user input selecting one of the overlaid contours 316
Save the selected segmentation contour to memory

END

FIG. 3

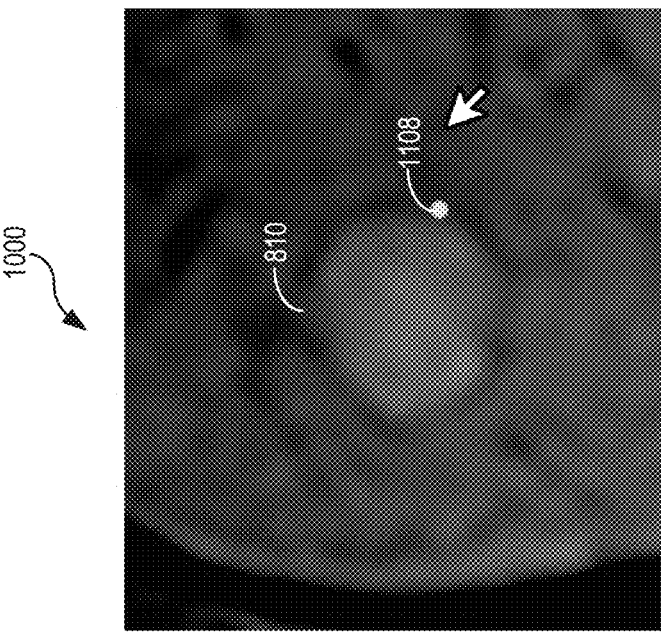
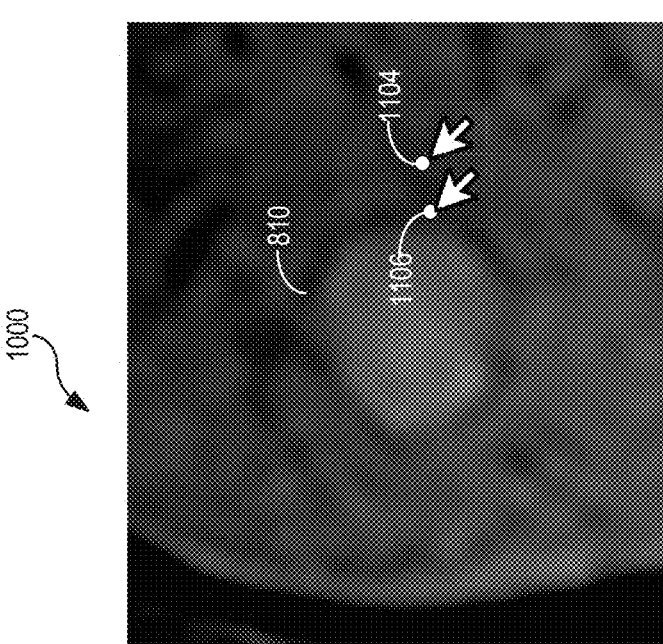
FIG. 11

METHODS AND SYSTEMS FOR IMAGE ANNOTATION AND SEGMENTATION

FIELD

Embodiments of the subject matter disclosed herein relate to image processing, and more particularly to image annotation and segmentation.

BACKGROUND

Clinical decisions may be derived from an analysis of a set or sets of data. In the radiology domain, this may typically involve analysis of regions of interest from medical image data, which may include 2D or 3D medical images, such as images of organs (kidney, liver, spleen, etc.), blood vessels, bones, and the like. Medical image analysis may be performed at the request of a referring physician for a specific purpose; this purpose may include detection, assessment, and/or monitoring progression of anatomical abnormalities like lesions, tumors, aneurysms, atrophies, and so on.

In order to access these regions of interest of the medical image data and perform the desired analysis, data corresponding to these regions may first be accurately and robustly separated from other data. A segmentation process may be employed to separate the regions of interest so as to increase usability in diagnosis, treatment planning, and treatment monitoring.

BRIEF DESCRIPTION

In one embodiment, a method comprises obtaining three-dimensional (3D) multi-volume imaging data, the 3D multi-volume imaging data comprising a plurality of registered image volumes; determining one or more positions of a user cursor within a first image of a first image volume of the plurality of registered image volumes; determining a contour point position corresponding to each of the one or more positions of the user cursor for two or more of the plurality of registered image volumes; generating two or more segmentation contours corresponding to the two or more of the plurality of registered image volumes; determining, via user input, a selected segmentation contour of the two or more segmentation contours; generating a 3D segmentation mask based at least in part on the selected segmentation contour; and saving the 3D segmentation mask to memory.

In another embodiment, a system comprises an imaging system configured to acquire three-dimensional (3D) multi-volume imaging data and a computing device communicably coupled to the imaging system, the computing device configured with instructions stored in non-transitory memory executable by a processor that, when executed, cause the processor to: obtain a 3D multi-volume imaging dataset from an imaging archive, wherein the 3D multi-volume imaging dataset comprises a plurality of registered image volumes each comprising a plurality of image slices; display an image slice of a first set of image slices of two or more image volumes of the plurality of registered image volumes within a graphical user interface (GUI) of a display device communicably coupled to the computing device; determine two or more positions of a user cursor within a first image slice of a first image volume in response to user input; determine contour points within two or more image slices corresponding to two or more of the plurality of registered image volumes based on the two or more positions of the user cursor within the first image slice; generate two or more segmentation contours, wherein each of the two or more segmentation contours corresponds to one of the two or more image slices and comprise respective pluralities of contour points; select, in response to user input, a selected segmentation contour of the two or more segmentation contours; generate, based on the selected contour, a 3D segmentation mask; and save the 3D segmentation mask to non-transitory memory.

In yet another embodiment, a method comprises determining a position of a user cursor within a first image of a first image volume of a plurality of image volumes of a 3D multi-volume imaging dataset; generating a geodesic propagation around the position of the user cursor within two or more images of two or more corresponding image volumes of the plurality of image volumes; determining one or more gradients within the geodesic propagation of each of the two or more images, wherein the one or more gradients correlate to an edge of a region of interest; defining the edge of the region of interest within the geodesic propagation of each of the two or more images based on the one or more gradients; determining a point of the edge closest to the position of the user cursor within each of the two or more images; and saving the point as one of a plurality of points of a segmentation contour for each of the two or more images.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present disclosure will be better understood from reading the following description of non-limiting embodiments, with reference to the attached drawings, wherein below:

FIG. 3 shows a flowchart illustrating a method for computing a segmentation contour.

FIG. 11 shows the region of interest of the multi-parametric imaging of FIG. 8 with multiple user cursors and a contour point.

DETAILED DESCRIPTION

Figure 1:
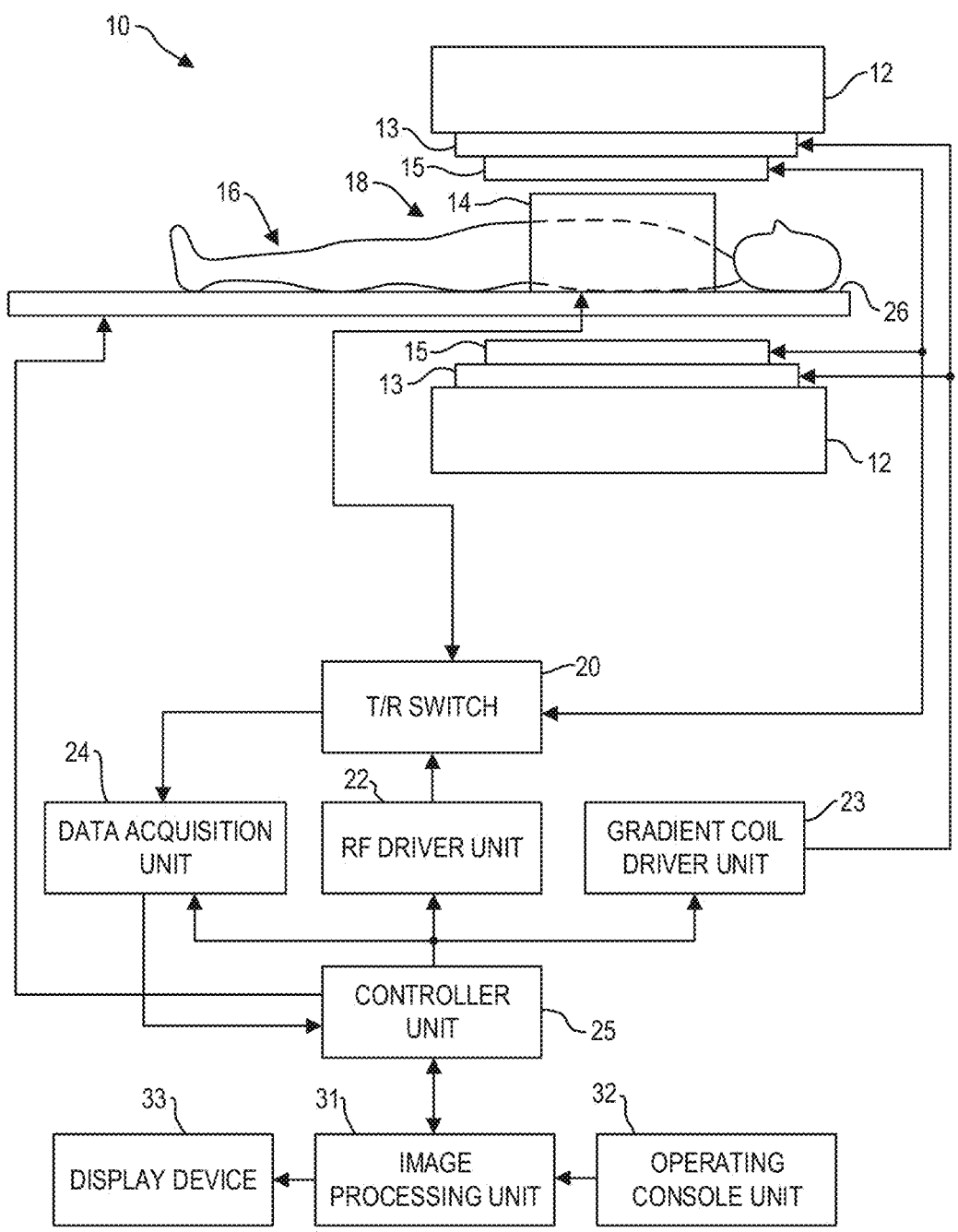
FIG. 1 shows a block diagram of an imaging system according to an embodiment of the disclosure.

The following description relates to various embodiments for methods and systems for annotation and segmentation of three-dimensional (3D) multi-volume medical image data. Image segmentation is a sub-domain of image processing which aims at grouping similar regions or segments of an image. Image segmentation may include partitioning a digital image into distinct components (in other words, partitioning the digital image into image segments, with each image segment being a collection of pixels or voxels), and may be utilized in order to simplify and/or change the representation of an image into something that is more meaningful and easier to analyze (e.g., by a referring physician). Image segmentation may be used in a variety of applications, including use in medical imaging. During analysis of medical image data, which may be two-dimensional (2D), 3D, or in some examples, 3D datasets with multiple volumes (e.g., multi-parametric imaging data or multi-phase imaging data), it may be useful to apply segmentation to the medical image data in order to allow for easier characterization of certain anatomical features (e.g., organs, lesions, etc.) by a referring physician for diagnosis, analysis, and the like. Segmentation is implementable on medical images captured using a variety of modalities, including magnetic resonance imaging (MRI), computing tomography (CT), positron emission tomography (PET), ultrasound, and more.

Current tools for image segmentation of 3D imaging data, such as manual annotation workflow tools like "Paint on Slice", utilize user inputs to 2D slices of the 3D imaging data, such as contours manually drawn around a region of interest, to segment the region of interest. In such examples, contours may be manually drawn onto each 2D slice of the 3D imaging data and then an interpolation process is applied to generate a 3D segmentation from the plurality of contours. Manually inputted contours as is utilized for manual annotation workflow tools may result in a high degree of variability of annotation between contours as only the user inputs are used to determine the contours and segmentations.

Because of the high variability with manual annotation segmentation methods, various methods addressing this issue have been developed. In some examples, closest gradient detection and/or edge detection algorithms are used in conjunction with manual inputs to generate contours on 2D slices of 3D imaging data. While these methods reduce variability from manual input, variability may remain in gradient and edge detection that leads to inaccurate segmentations based on variability in scanning acquisition, sequence parameters, etc. that affect the images and regions of interest therewithin.

Further, multi-volume imaging data, as is generated by multi-parametric and/or multi-phase imaging methods, which increase available data of regions of interest, may demand individual segmentation for each sequence or phase separately despite being of the same 3D imaging dataset, wherein the data set includes a plurality of registered image volumes of the same field of view. Multi-parametric imaging data, such as multi-parametric MRIs, CTs, ultrasounds, and the like, may combine a plurality of imaging parameters (e.g., sequences) for a set of 3D medical imaging data. For example, a multi-parametric MRI may include data of multiple sequences acquired of a particular field of view, such as a T1-weighted sequence, a T2-weighted sequence, a T1 contrast enhanced (T1CE) sequence, a fluid attenuated inversion recovery (FLAIR) sequence, a diffusion weighted imaging (DWI) sequence, among many others. Multi-phase imaging data include multiple images taken of a target anatomy at various points in time, typically as intravenous contrast dye moves through the circulatory system. As an example, a multi-phase liver CT may include a non-contrasted phase image, an arterial phase image (e.g., late arterial phase), a portal venous phase image, and a delayed phase image, wherein each image is acquired at different times when the contrast dye is at a particular enhancement for a specified area. For example, for the arterial phase, peak aortic attenuation may be seen with minimal liver enhancement while, for the portal venous phase, peak liver parenchyma and portal and hepatic vein enhancement may be seen.

In some examples, variations in anatomy placement within the field of view for different sequences/phases may occur as a result of periodic and/or non-periodic motion (e.g., breathing, skeletomuscular movement, etc.). The multiple volumes of the 3D imaging dataset may be registered via a translational volume registration method, a rigid volume registration method, a non-rigid volume registration method, or other type of volume registration method. Registration is the process of aligning different sets of spatial data (e.g., image volumes) by determining proper geometrical transformation between them. Registration of the multiple image volumes may allow for compensation of periodic and/or non-periodic motion by adjusting position and orientation until mutual information between the multiple image volumes until correlated.

In this way, multi-volume imaging data that includes multiple image volumes of the same target anatomy with different parameters or at different times may provide a fourth dimension to 3D imaging datasets, whereby a lesion or other region of interest may be imaged either in various manners (e.g., sequences of multi-parametric imaging) and/or at various times (e.g., phases of multi-phase imaging), providing increased information and imagery of the region of interest. As noted, in order to segment and/or annotate multi-volume imaging data, annotation and segmentation may be done for each of the volumes individually, as in some examples a lesion or region of interest that is to be segmented may appear differently in different volumes, therefore consuming increased amounts of time for a user as well as increased processing power.

Thus, embodiments of methods and systems are disclosed herein for annotation and segmentation of 3D multi-volume medical imaging data that addresses the aforementioned issues. As will be explained in more detail below, the embodiments disclosed herein may utilize images of 3D multi-volume, e.g., multi-parametric and/or multi-phase, imaging data upon which a user may provide annotation inputs to indicate one or more regions to be included in a segmentation mask. A position of a user cursor within a first 2D slice of a first volume of the 3D multi-volume imaging data may be located and, via determination of a closest gradient to the user cursor within a defined geodesic propagation area for each of two or more image slices of two or more corresponding, a position of a point of a segmentation contour (e.g., a contour point) may be determined for each of the volumes of the multi-volume data. A plurality of user cursor points for the first 2D slice of the first volume may define a plurality of contour points for each of the image volumes of the 3D multi-volume imaging data and may therefore define segmentation contours for each volume. One or all of the generated segmentation contours may be saved for the particular slice and a plurality of selected segmentation contours for different slices may be used to generate a 3D segmentation mask.

Thus, according to the embodiments disclosed herein, the issues described above may be addressed via a segmentation process including determining segmentation contours for each of a plurality of volumes of a 3D multi-volume imaging dataset from user cursor positions within one of the plurality of volumes. In this way, the region of interest that is segmented may include data of multiple parameters or phases, increasing the accuracy of annotation and segmentation. Further, while examples are presented herein relating to segmenting 3D images/volumetric data, it should be appreciated that the segmentation process described herein may be applied to 2D images, 3D images/renderings, and other types of medical images.

Figure 2:
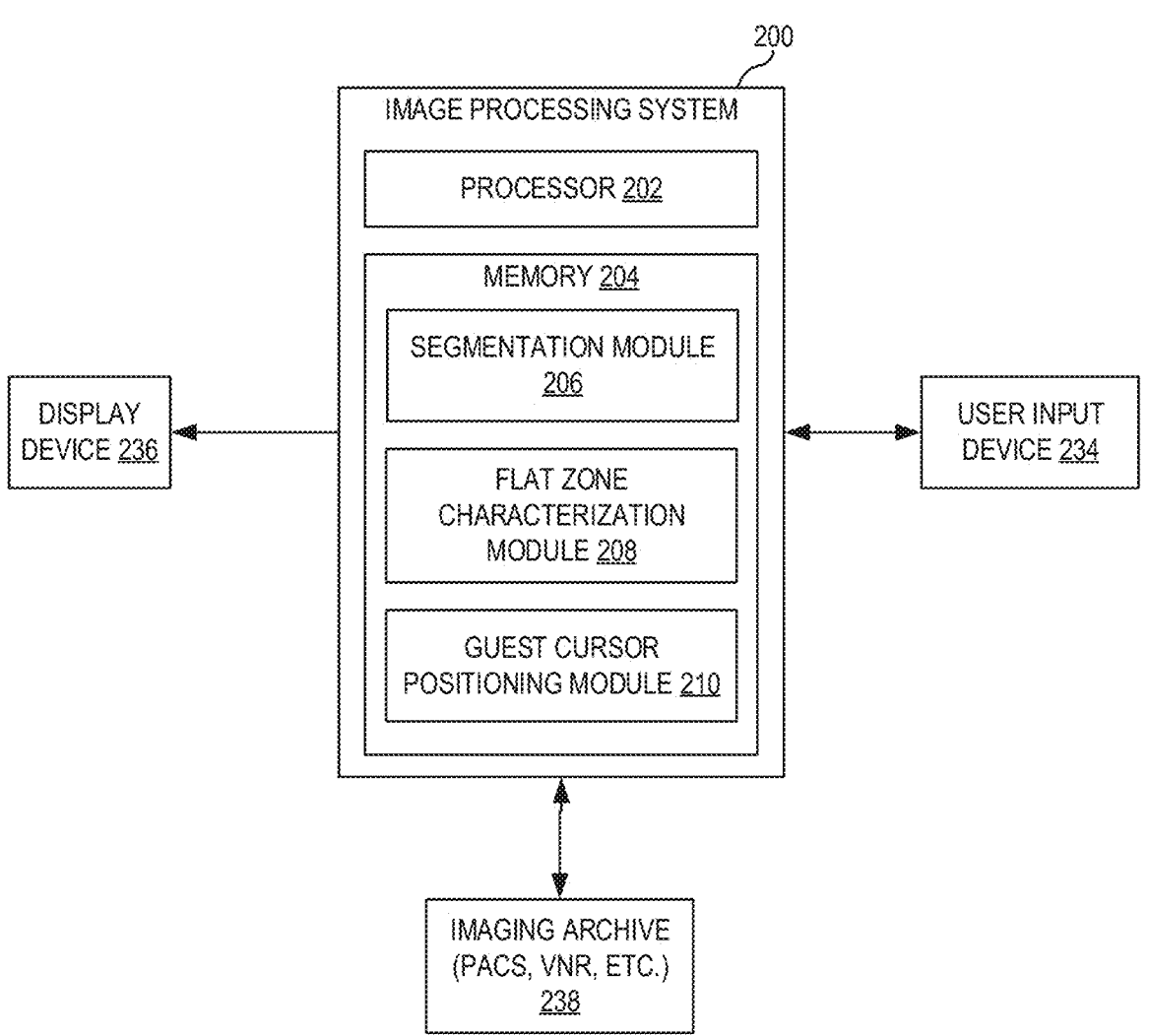
FIG. 2 shows a block diagram of an image processing system according to an embodiment of the disclosure.
Figure 4:
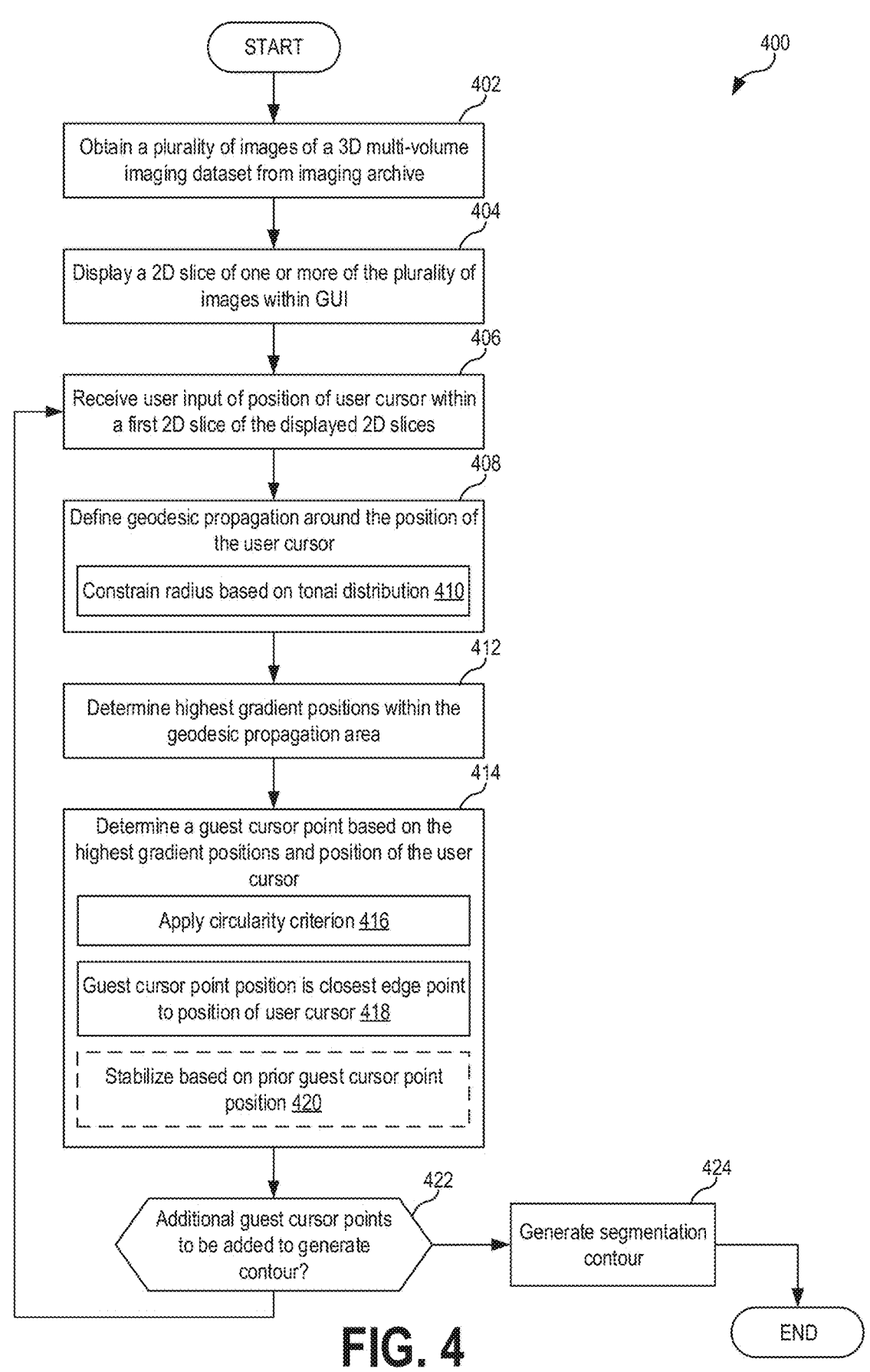
FIG. 4 shows a flowchart illustrating a method for segmenting a 2D region of interest from one or more images.
Figure 5:
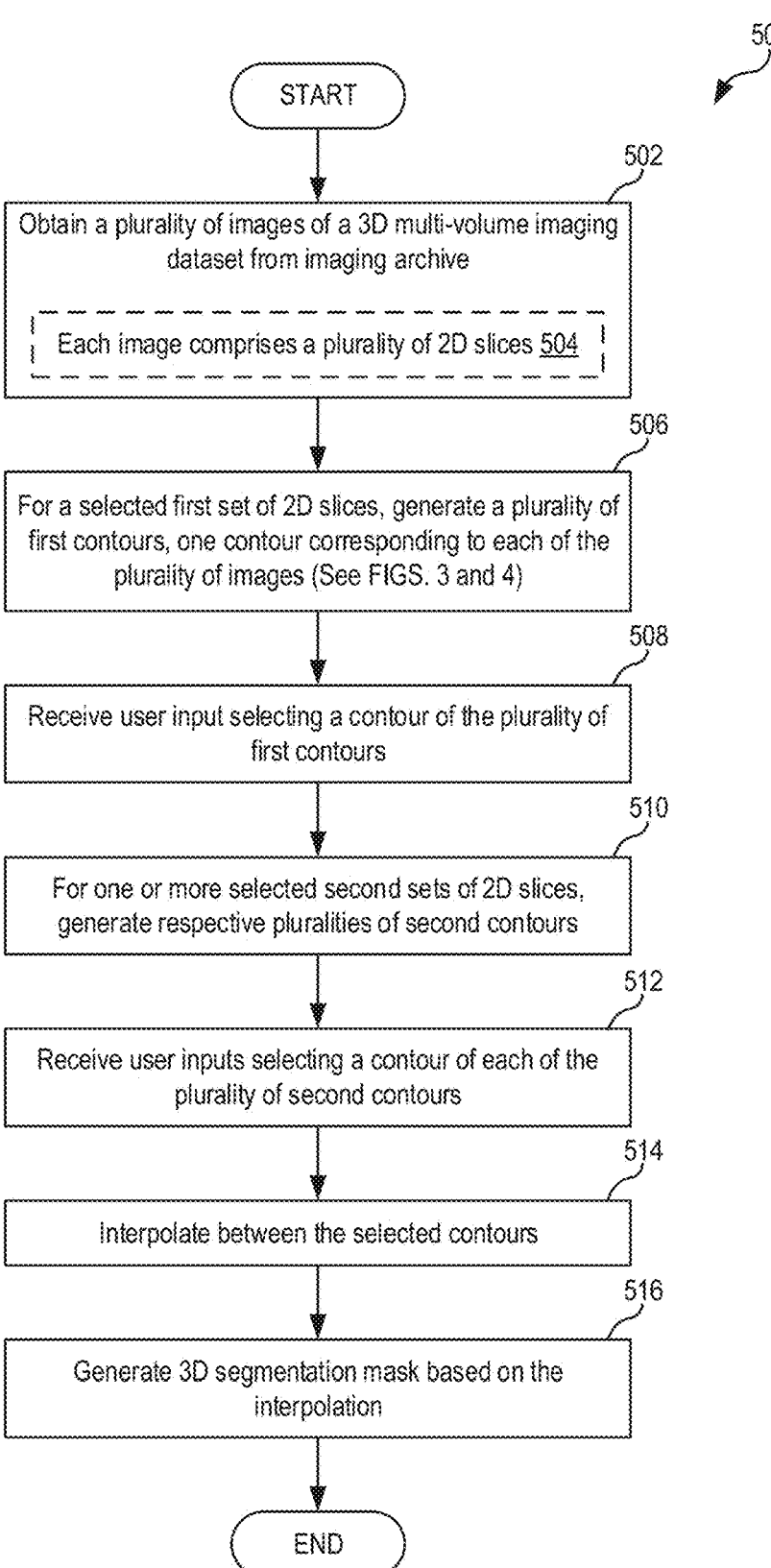
FIG. 5 shows a flowchart illustrating a method for generating a 3D segmentation.
Figure 6:
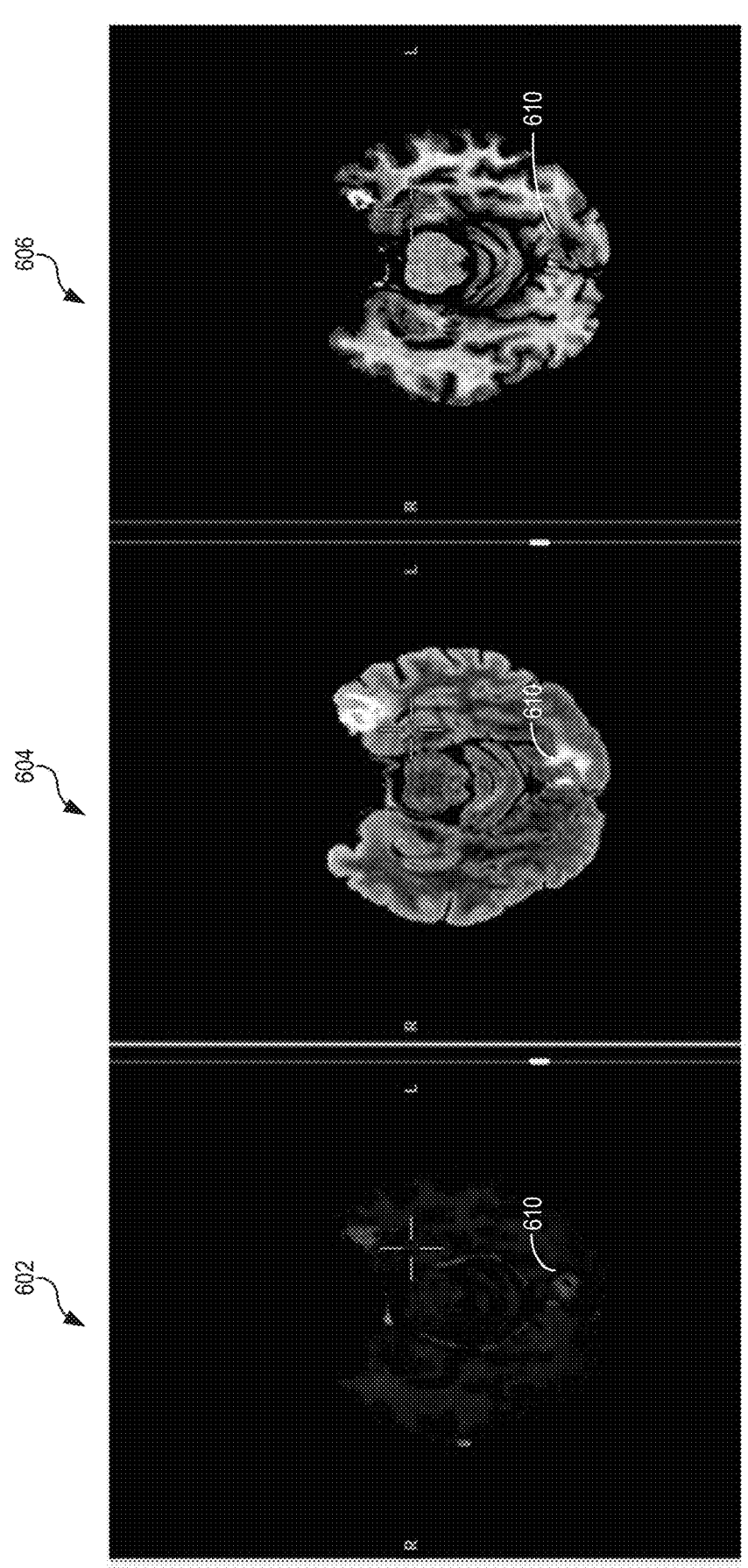
FIG. 6 shows example images of multi-parametric imaging data.
Figure 7:
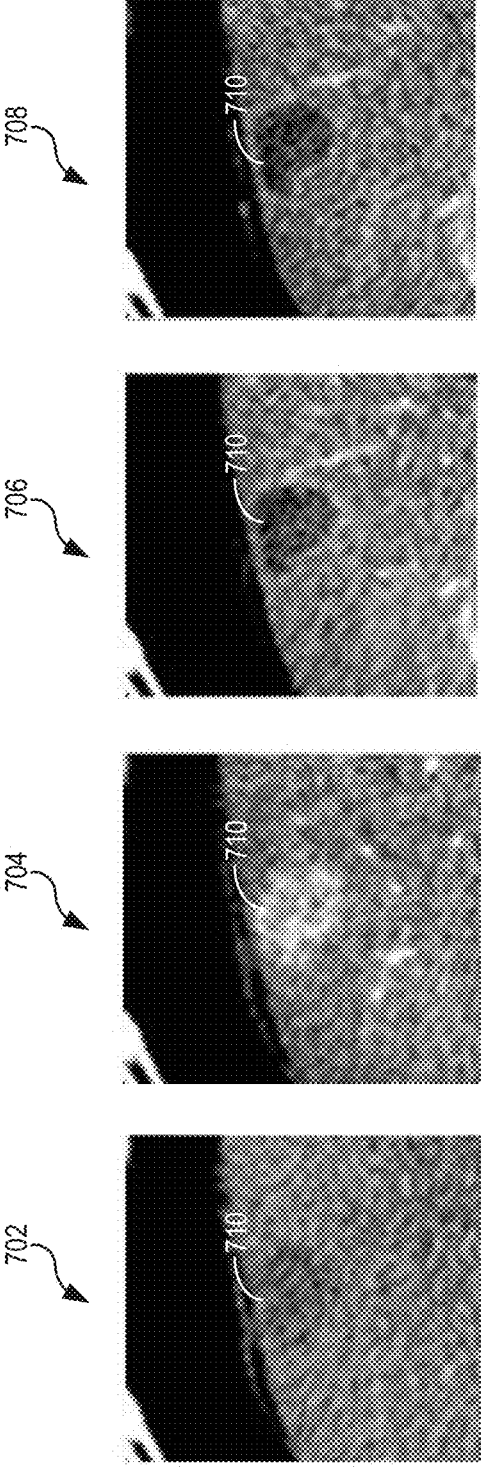
FIG. 7 shows example images of multi-phase imaging data.
Figure 8:
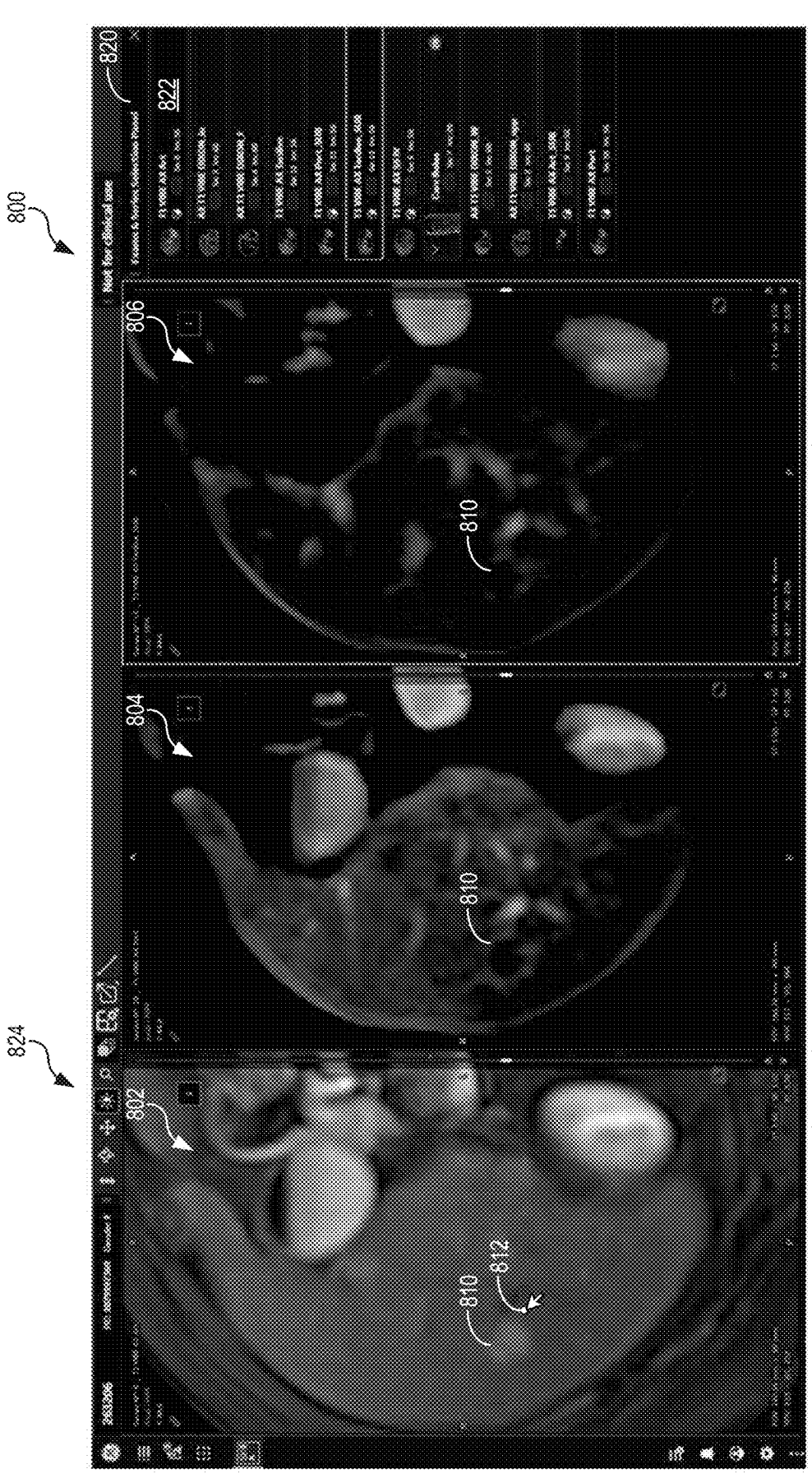
FIG. 8 shows an example graphical user interface (GUI) with multi-parametric imaging and a user cursor displayed therein.
Figure 9:
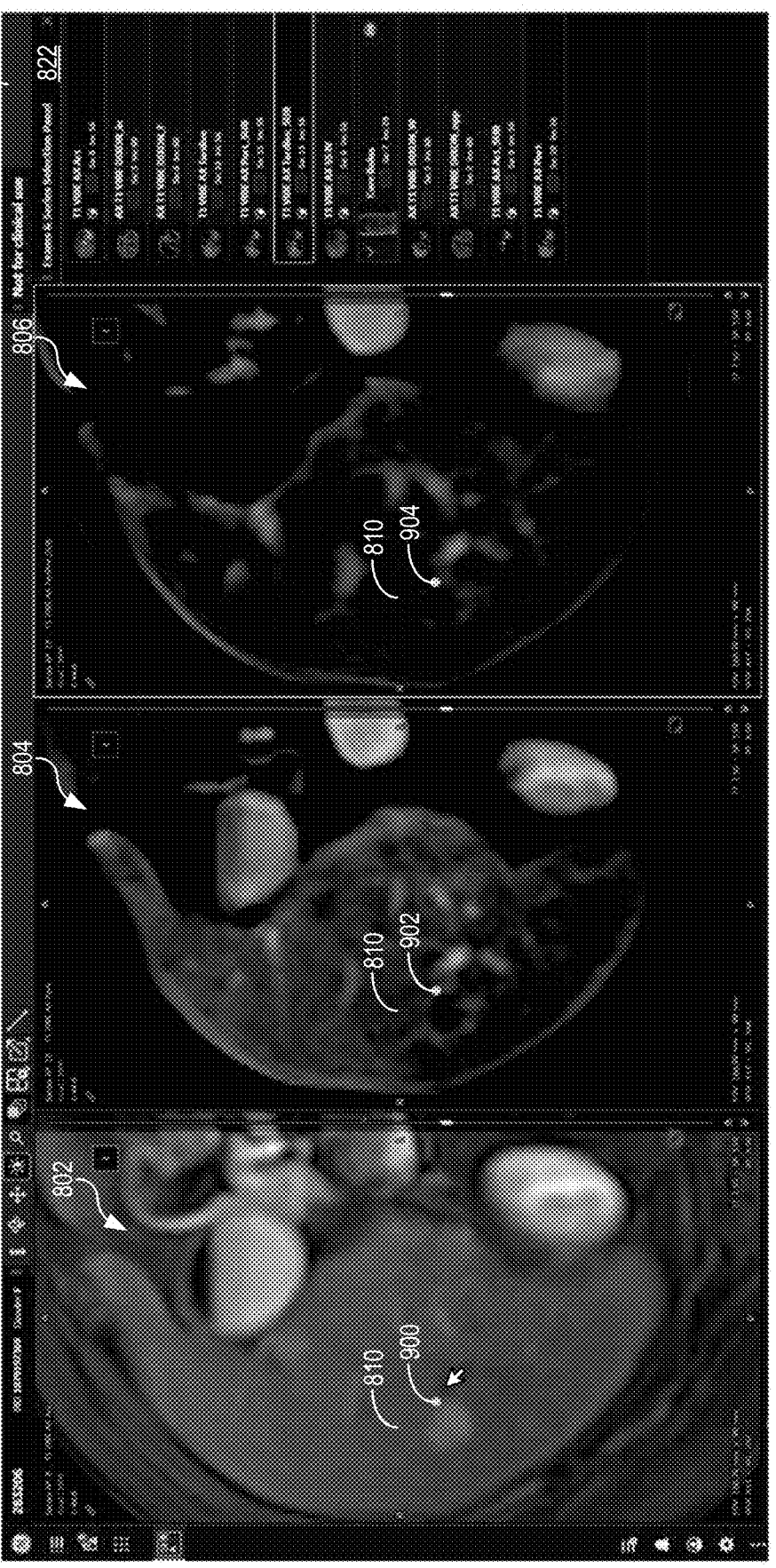
FIG. 9 shows the GUI of FIG. 8 with a contour point displayed.
Figure 10:
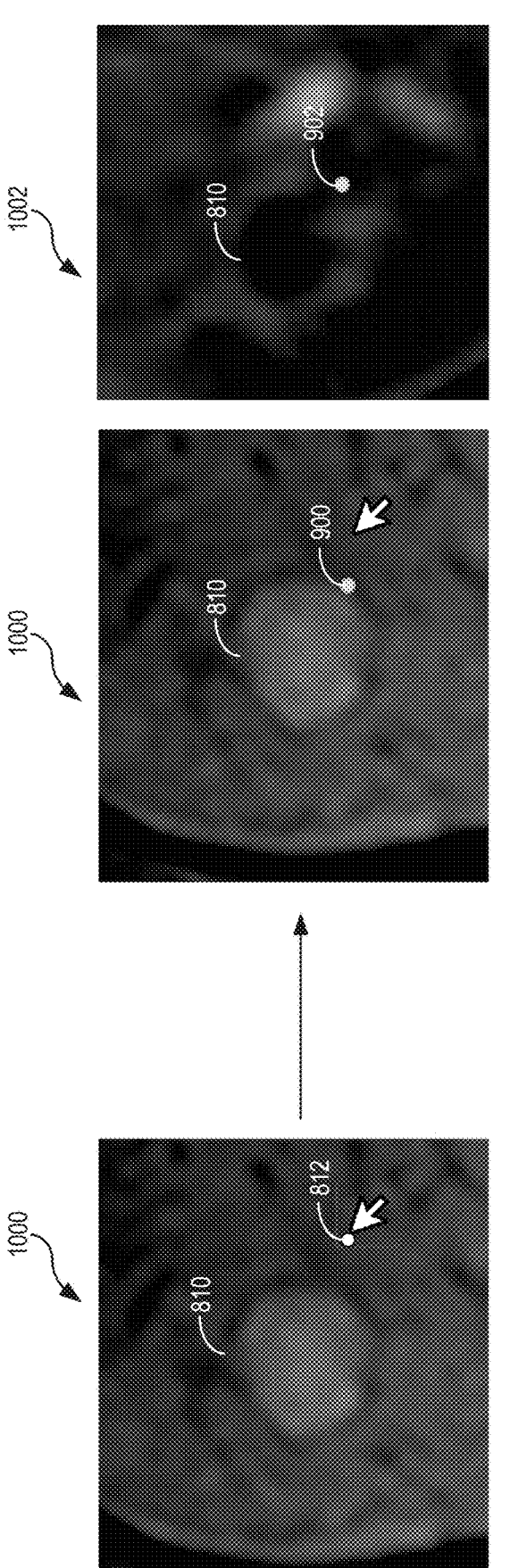
FIG. 10 shows a region of interest of the multi-parametric imaging of FIG. 8 with the user cursor and the contour point.
Figure 12:
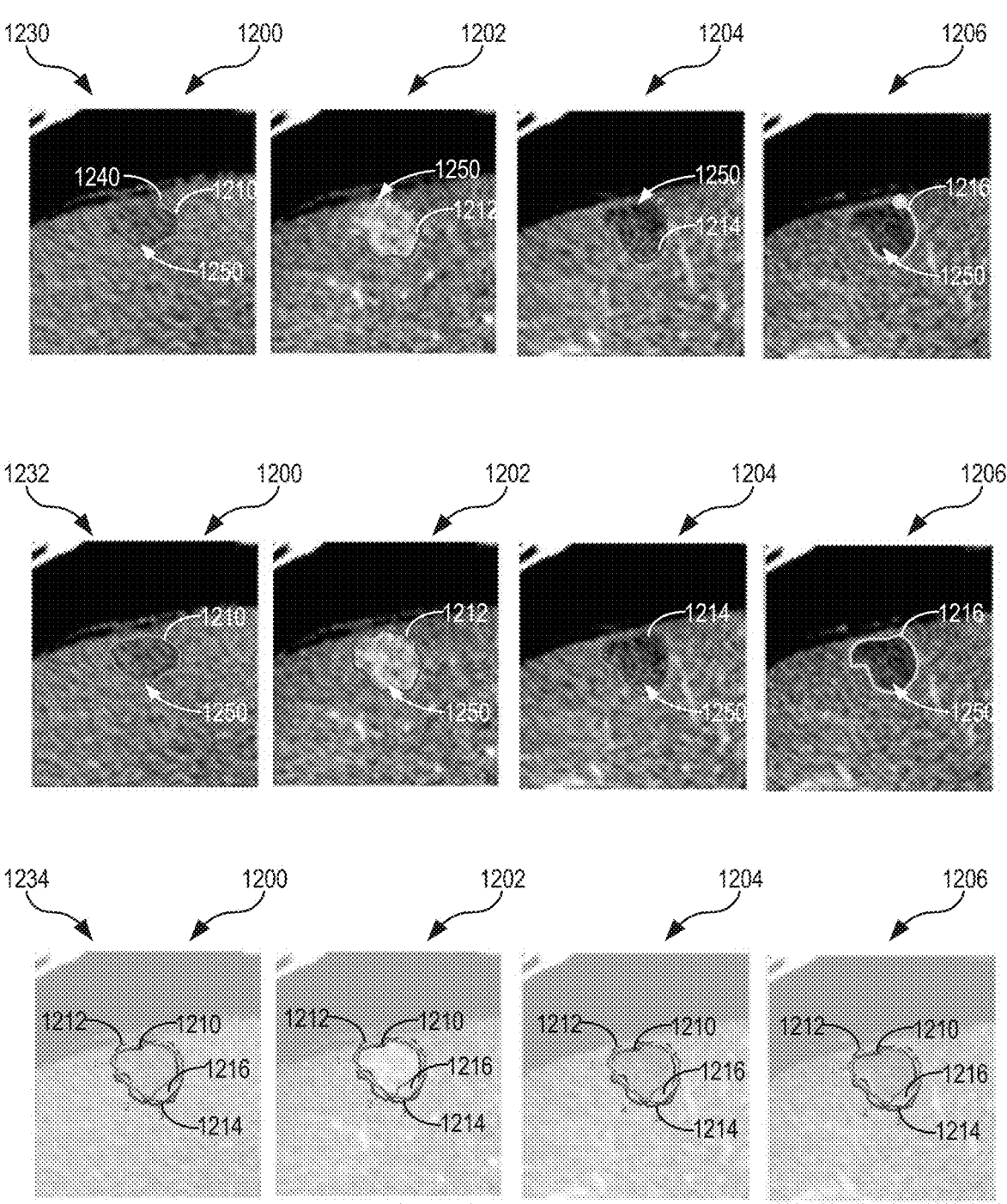
FIG. 12 shows example segmentation contours for each of a plurality of images of multi-phase imaging data.
Figure 13:
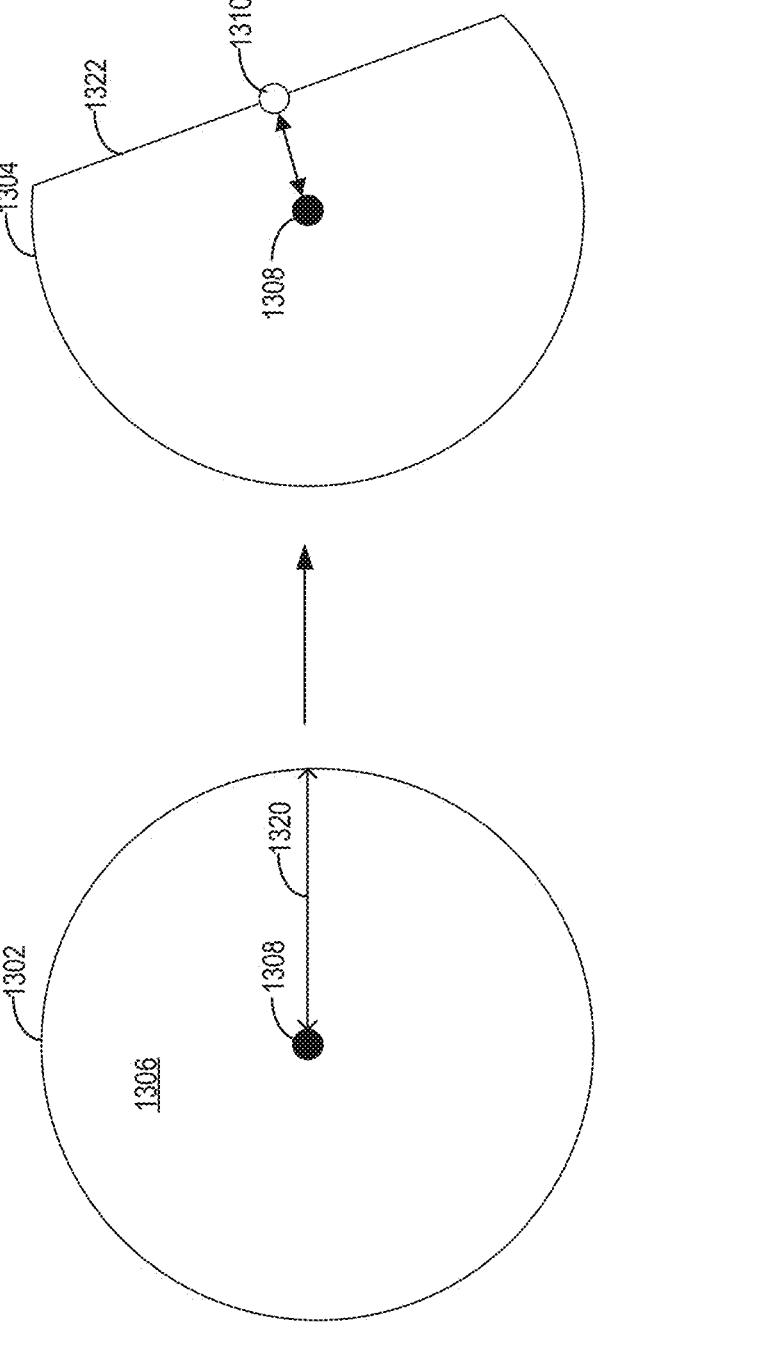
FIG. 13 shows a diagram of a flat zone with user cursors and a resultant contour point.
Figure 14:
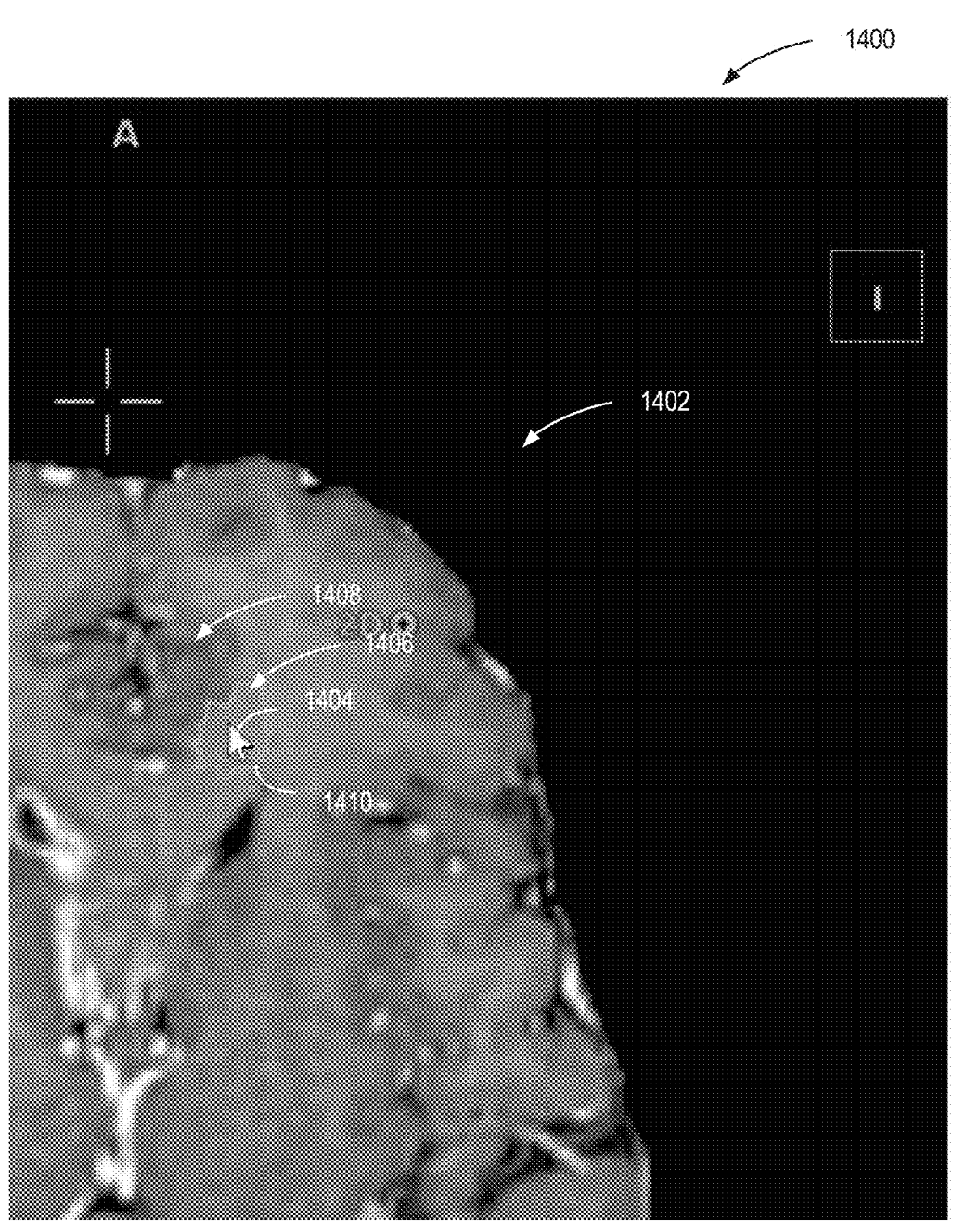
FIG. 14 shows an example GUI with a user cursor positioned in a first position within a medical image displayed therein.
Figure 15:
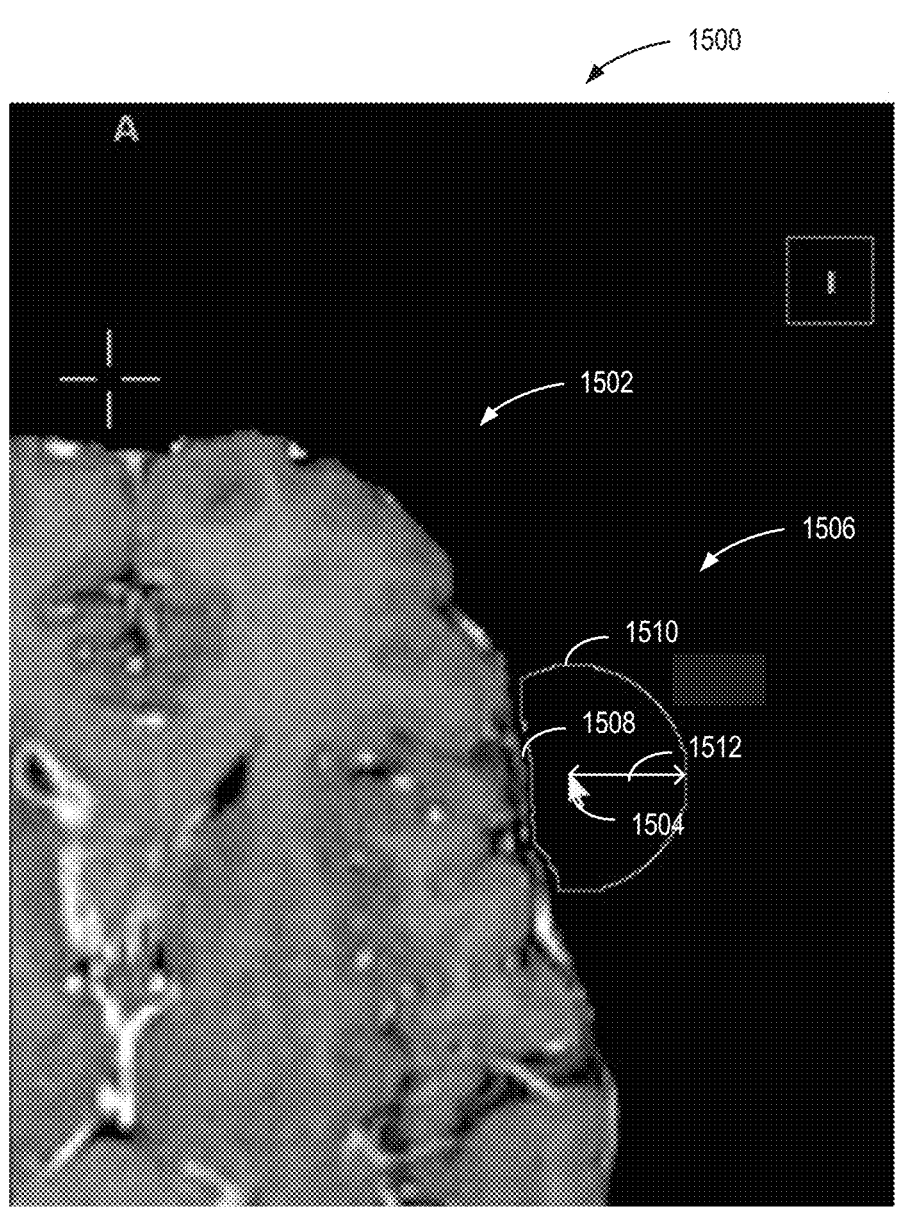
FIG. 15 shows the GUI with the user cursor positioned in a second position within the medical image.

Embodiments of the present disclosure will now be described, by way of example, with reference to the figures. FIG. 1 illustrates an exemplary imaging system that may be used to acquire 3D multi-volume imaging data. FIG. 2 shows a block diagram of an image processing system that may be a part of or otherwise communicatively coupled to the imaging system. FIGS. 3-5 illustrate methods for determining a segmentation contour of multi-volume imaging data, determining points of a segmentation contour, and generating a 3D segmentation mask from a plurality of segmentation contours, respectively. FIGS. 6-7 show example images of multi-volume imaging data, FIG. 6 showing an example of multi-parametric imaging data and FIG. 7 showing an example of multi-phase imaging data. FIG. 8 shows an example graphical user interface (GUI) displaying a plurality of images of multi-volume data to be segmented with a user cursor in a first position. FIG. 9 shows the GUI of FIG. 8 with a point for each volume determined from the first position of the user cursor. FIGS. 10 and 11 show a region of interest to be segmented with a user cursor and corresponding points in respective image volumes. FIG. 12 shows a plurality of segmentation contours corresponding to a plurality of image volumes. FIG. 13 shows a diagram of a flat zone within a geodesic propagation used to determine a point of a segmentation contour. FIGS. 14 and 15 show an example GUI with a user cursor positioned within an image in various positions.

Turning now to FIG. 1, an illustration of an exemplary imaging system as may be used to generate 3D multi-volume imaging data is shown. As an example, an MRI system 10 includes a magnetostatic field magnet unit 12, a gradient coil unit 13, an RF coil unit 14, an RF body or volume coil unit 15, a transmit/receive (T/R) switch 20, an RF driver unit 22, a gradient coil driver unit 23, a data acquisition unit 24, a controller unit 25, a patient bed or table 26, an image processing unit 31, an operating console unit 32, and a display device 33. In some embodiments, the RF coil unit 14 is a local coil typically placed proximate to the anatomy of interest of a subject 16. Herein, the RF body coil unit 15 is a transmit coil that transmits RF signals, and the local surface RF coil unit 14 receives the MR signals. As such, the transmit body coil (e.g., RF body coil unit 15) and the surface receive coil (e.g., RF coil unit 14) are separate but electromagnetically coupled components. The MRI system 10 transmits electromagnetic pulse signals to the subject 16 placed in an imaging space 18 with a static magnetic field formed to perform a scan for obtaining magnetic resonance signals from the subject 16. One or more images of the subject 16 can be reconstructed based on the magnetic resonance signals thus obtained by the scan.

The magnetostatic field magnet unit 12 includes, for example, an annular superconducting magnet, which is mounted within a toroidal vacuum vessel. The magnet defines a cylindrical space surrounding the subject 16 and generates a constant primary magnetostatic field $B_0$.

The MRI system 10 also includes a gradient coil unit 13 that forms a gradient magnetic field in the imaging space 18 so as to provide the magnetic resonance signals received by the RF coil arrays with three-dimensional positional information. The gradient coil unit 13 includes three gradient coil systems, each of which generates a gradient magnetic field along one of three spatial axes perpendicular to each other, and generates a gradient field in each of a frequency encoding direction, a phase encoding direction, and a slice selection direction in accordance with the imaging condition. More specifically, the gradient coil unit 13 applies a gradient field in the slice selection direction (or scan direction) of the subject 16, to select the slice; and the RF body coil unit 15 or the local RF coil arrays may transmit an RF pulse to a selected slice of the subject 16. The gradient coil unit 13 also applies a gradient field in the phase encoding direction of the subject 16 to phase encode the magnetic resonance signals from the slice excited by the RF pulse. The gradient coil unit 13 then applies a gradient field in the frequency encoding direction of the subject 16 to frequency encode the magnetic resonance signals from the slice excited by the RF pulse.

The RF coil unit 14 is disposed, for example, to enclose the region to be imaged of the subject 16. In some examples, the RF coil unit 14 may be referred to as the surface coil or the receive coil. In the static magnetic field space or imaging space 18 where a static magnetic field $B_0$ is formed by the magnetostatic field magnet unit 12, the RF coil unit 15 transmits, based on a control signal from the controller unit 25, an RF pulse that is an electromagnet wave to the subject 16 and thereby generates a high-frequency magnetic field $B_1$. This excites a spin of protons in the slice to be imaged of the subject 16. The RF coil unit 14 receives, as a magnetic resonance signal, the electromagnetic wave generated when the proton spin thus excited in the slice to be imaged of the subject 16 returns into alignment with the initial magnetization vector. In some embodiments, the RF coil unit 14 may transmit the RF pulse and receive the MR signal. In other embodiments, the RF coil unit 14 may only be used for receiving the MR signals, but not transmitting the RF pulse.

The RF body coil unit 15 is disposed, for example, to enclose the imaging space 18, and produces RF magnetic field pulses orthogonal to the main magnetic field $B_0$ produced by the magnetostatic field magnet unit 12 within the imaging space 18 to excite the nuclei. In contrast to the RF coil unit 14, which may be disconnected from the MRI system 10 and replaced with another RF coil unit, the RF body coil unit 15 is fixedly attached and connected to the MRI system 10. Furthermore, whereas local coils such as the RF coil unit 14 can transmit to or receive signals from only a localized region of the subject 16, the RF body coil unit 15 generally has a larger coverage area. The RF body coil unit 15 may be used to transmit or receive signals to the whole body of the subject 16, for example. Using receive-only local coils and transmit body coils provides a uniform RF excitation and good image uniformity at the expense of high RF power deposited in the subject. For a transmit-receive local coil, the local coil provides the RF excitation to the region of interest and receives the MR signal, thereby decreasing the RF power deposited in the subject. It should be appreciated that the particular use of the RF coil unit 14 and/or the RF body coil unit 15 depends on the imaging application.

The T/R switch 20 can selectively electrically connect the RF body coil unit 15 to the data acquisition unit 24 when operating in receive mode, and to the RF driver unit 22 when operating in transmit mode. Similarly, the T/R switch 20 can selectively electrically connect the RF coil unit 14 to the data acquisition unit 24 when the RF coil unit 14 operates in receive mode, and to the RF driver unit 22 when operating in transmit mode. When the RF coil unit 14 and the RF body coil unit 15 are both used in a single scan, for example if the RF coil unit 14 is configured to receive MR signals and the RF body coil unit 15 is configured to transmit RF signals, then the T/R switch 20 may direct control signals from the RF driver unit 22 to the RF body coil unit 15 while directing received MR signals from the RF coil unit 14 to the data acquisition unit 24. The coils of the RF body coil unit 15 may be configured to operate in a transmit-only mode or a transmit-receive mode. The coils of the local RF coil unit 14 may be configured to operate in a transmit-receive mode or a receive-only mode.

The RF driver unit 22 includes a gate modulator (not shown), an RF power amplifier (not shown), and an RF oscillator (not shown) that are used to drive the RF coils (e.g., RF coil unit 15) and form a high-frequency magnetic field in the imaging space 18. The RF driver unit 22 modulates, based on a control signal from the controller unit 25 and using the gate modulator, the RF signal received from the RF oscillator into a signal of predetermined timing having a predetermined envelope. The RF signal modulated by the gate modulator is amplified by the RF power amplifier and then output to the RF coil unit 15.

The gradient coil driver unit 23 drives the gradient coil unit 13 based on a control signal from the controller unit 25 and thereby generates a gradient magnetic field in the imaging space 18. The gradient coil driver unit 23 includes three systems of driver circuits (not shown) corresponding to the three gradient coil systems included in the gradient coil unit 13.

The data acquisition unit 24 includes a pre-amplifier (not shown), a phase detector (not shown), and an analog/digital converter (not shown) used to acquire the magnetic resonance signals received by the RF coil unit 14. In the data acquisition unit 24, the phase detector phase detects, using the output from the RF oscillator of the RF driver unit 22 as a reference signal, the magnetic resonance signals received from the RF coil unit 14 and amplified by the pre-amplifier, and outputs the phase-detected analog magnetic resonance signals to the analog/digital converter for conversion into digital signals. The digital signals thus obtained are output to the image processing unit 31.

The MRI apparatus 10 includes a table 26 for placing the subject 16 thereon. The subject 16 may be moved inside and outside the imaging space 18 by moving the table 26 based on control signals from the controller unit 25.

The controller unit 25 includes a computer and a recording medium on which a program to be executed by the computer is recorded. The program when executed by the computer causes various parts of the apparatus to carry out operations corresponding to pre-determined scanning. The recording medium may comprise, for example, a ROM, flexible disk, hard disk, optical disk, magneto-optical disk, CD-ROM, or non-volatile memory card. The controller unit 25 is connected to the operating console unit 32 and processes the operation signals input to the operating console unit 32 and furthermore controls the table 26, RF driver unit 22, gradient coil driver unit 23, and data acquisition unit 24 by outputting control signals to them. The controller unit 25 also controls, to obtain a desired image, the image processing unit 31 and the display device 33 based on operation signals received from the operating console unit 32.

The operating console unit 32 includes user input devices such as a touchscreen, keyboard and a mouse. The operating console unit 32 is used by an operator, for example, to input such data as an imaging protocol and to set a region where an imaging sequence is to be executed. The data about the imaging protocol and the imaging sequence execution region are output to the controller unit 25.

The image processing unit 31 includes a computing device and a recording medium on which a program to be executed by the computing device to perform predetermined data processing is recorded. The image processing unit 31 is connected to the controller unit 25 and performs data processing based on control signals received from the controller unit 25. The image processing unit 31 is also connected to the data acquisition unit 24 and generates spectrum data by applying various image processing operations to the magnetic resonance signals output from the data acquisition unit 24.

The display device 33 may display one or more images within a GUI on the display screen of the display device based on control signals received from the controller unit 25. The display device 33 displays, for example, an image regarding an input item about which the operator inputs operation data from the operating console unit 32. The display device 33 also displays a 2D slice image or 3D image of the subject 16 generated by the image processing unit 31.

The MRI system 10 may be configured for multi-volume imaging, e.g., multi-parametric and/or multi-phase imaging, wherein multiple imaging sequences and/or phases are imaged during a single imaging session. Resultant MRI imaging data may include images from each of the imaged sequences and/or phases, wherein the MRI imaging data is subdivided into specified sequences and/or phases. Each of the specified sequences and/or phases may define a plurality of 2D slices thereof, each of the 2D slices particular to a z-coordinate of the MRI imaging data. A z-coordinate may therefore define a plurality of 2D slices, one from each of the specified sequences and/or phases.

Though a MRI system is described by way of example, it should be understood that the present techniques may be applied to images acquired using other imaging systems capable of multi-parametric, multi-phase, or other type of multi-volume imaging, such as CT, tomosynthesis, PET, ultrasound, and so forth. The present discussion of an MRI imaging modality is provided merely as an example of one suitable imaging modality.

Referring to FIG. 2, an image processing system 200 is shown. In some embodiments, the image processing system 200 may be incorporated into an imaging system, such as the MRI system 10. For example, the image processing system 200 may be the image processing unit 31 of the MRI system 10. However, in other embodiments, the image processing system 200 may be disposed at a device (e.g., a server, edge device, etc.) communicably coupled to the imaging system via wired and/or wireless connections. In some examples, at least a portion of image processing system 200 may be disposed at a separate device (e.g., a workstation) which can receive images from the imaging system or from a storage device which stores the images generated by the imaging system and/or other additional imaging systems. Image processing system 200 may be communicatively coupled to a user input device 234, a display device 236, and an imaging archive 238. The user input device 234 may, in some examples, be included in the operator console unit 32 of FIG. 1 and the display device 236 may be the display device 33 of FIG. 1.

Image processing system 200 may include a processor 202 configured to execute machine readable instructions stored in non-transitory memory 204. Processor 202 may be single core or multi-core, and the programs executed thereon may be configured for parallel or distributed processing. In some embodiments, the processor 202 may optionally include individual components that are distributed throughout two or more devices, which may be remotely located and/or configured for coordinate processing. In some examples, one or more aspects of the processor 202 may be virtualized and executed by remotely-accessible networked computing devices configured in a cloud computing configuration.

In addition to the images directly provided by the image processing system 200, images may be further sourced from the imaging archive 238 communicatively coupled to the image processing system 200. The imaging archive 238 may comprise, for example, a picture archiving and communication system (PACS), a vendor neutral archive (VNA), or other suitable medical image database. The medical imaging archive may be hosted on a remote server configured to allow the image processing system 200 to access the plurality of medical images and patient data hosted thereon. In some examples, the plurality of medical images stored in the imaging archive 238 may be of different types, for example MRI images, CT images, ultrasound images, and more may all be stored in the imaging archive 238 for one or more patients.

Non-transitory memory 204 may store a segmentation module 206, a flat zone characterization module 208, and a contour point positioning module 210. The segmentation module 206 may obtain or otherwise determine one or more contours for a multi-volume imaging dataset, each of the one or more contours corresponding to a specified 2D slice of the imaging dataset. The segmentation module 206 may also interpolate between the one or more contours to define a 3D segmentation mask for a region of interest.

The flat zone characterization module 208 may analyze one or more images (e.g., 2D slices of 3D data, thick cut 3D data, 2D projected renderings, etc.) for pixel intensity, gradients, tonal distributions, and the like. The flat zone characterization module 208 may determine a geodesic propagation around a user cursor position and determine pixel intensities within the geodesic propagation area. Image gradient may be a change in the intensity in an image, and the highest gradient may be where the most change occurs between pixels. The highest gradient may, in some examples in which gradients are sharp, indicate an edge of a region of interest. In other examples in which the gradients are gradual or less sharp, one or more gradients that correlate to the edge of the region of interest may not be the highest gradients within the geodesic propagation. The flat zone characterization module 208 may thus store instructions to determine a gradient within the geodesic propagation for each displayed image for a given position of the user cursor that correlates to the edge of the region of interest, whether it is the highest gradient or other gradients. If one or more gradients are detected within the geodesic propagation area, a designated area may be determined that approximates an edge based on the detected gradients. If no gradients are detected, the area may be considered a flat zone, wherein all the pixels (or voxels) therein have the same or relatively the same (e.g., ±a specified noise) pixel intensity. If a flat zone is determined, the area may be a circle (for a 2D slice) or a sphere (for 3D data). When a gradient is detected or otherwise determined, the area may not be a circle, as will be described with respect to FIG. 13. Flat zone characterization and gradient determination may be performed by the flat zone characterization module 208 for each volume of a plurality of volumes of the 3D multi-volume imaging dataset based on a user cursor position provided to an imageslice of a single image volume.

The contour point positioning module 210 may obtain the data of flat zone characterization and gradients and store instructions for determining a position of a point, also referred to herein as a "contour point", corresponding to the user cursor position for each of the plurality of volumes. In some examples, the point may be one of a plurality of points of a segmentation contour corresponding to a respective image volume. The determined point may be a closest point of an edge of the designated area around the user cursor to the position of the user cursor. The closest point may be one of the determined correlated gradients, in some examples. Further, the contour point positioning module 210 may comprise data of a previously determined contour point to stabilize subsequent contour points of a particular segmentation contour.

In some embodiments, the non-transitory memory 204 may include components disposed at two or more devices, which may be remotely located and/or configured for coordinated processing. In some embodiments, one or more aspects of the non-transitory memory 204 may include remotely-accessible networked storage devices configured in a cloud computing configuration.

Turning now to FIG. 3, a flowchart illustrating a method 300 for determining and displaying a plurality of segmentation contours is shown. The method 300 will be described with relation to the systems depicted in FIGS. 1-2, but it should be understood that similar methods may be used with other systems without departing from the scope of this disclosure. The method 300 may be carried out via instructions stored in non-transitory memory of one or more computing devices. In some examples, the method 300 may be carried out by a computing device (e.g., the computing device that comprises the processor 202 of the image processing system 200 of FIG. 2) as well as a set of remote servers, also referred to herein as a cloud computing system, in communication with the computing device. The computing device may be in communication with an imaging archive (e.g., imaging archive 238).

At 302, the method 300 includes obtaining a plurality of images of a 3D multi-volume imaging dataset from the imaging archive. The multi-volume imaging dataset may be acquired via an imaging system (e.g., MRI system 10 of FIG. 1) configured for acquiring multi-volume data, such as multi-parametric imaging data and/or multi-phase imaging data. In some examples, the multi-volume imaging dataset that is to be segmented may be selected via user input. For example, a user may select a desired multi-volume imaging dataset to be segmented and may request, via user input, that the selected 3D multi-volume imaging dataset be segmented (e.g., by selecting a segmentation tab, tool, or the like). The 3D multi-volume imaging dataset may comprise a plurality of registered image volumes, each image volume from a different imaging sequence or phase taken of the same field of view and registered to each other as described above. In some examples, each of the plurality of registered image volumes may be partitioned into a plurality of 2D slices. Each of the 2D slices may be specific to a particular coordinate according to an axis in which they were obtained (e.g., a z-coordinate for an axial view). In some examples, the plurality of 2D slices for each of the plurality of registered image volumes may have the same set coordinates. In other examples, the set of coordinates of the plurality of 2D slices for one or more of the plurality of registered image volumes may different from the other pluralities of 2D slices due to sequencing parameters, acquisition parameters, or the like. The plurality of images obtained may be entire imaging volumes.

At 304, the method 300 includes displaying an image slice of one or more of the plurality of images in a GUI. In some examples, the displayed image slices may be 2D slices. In other examples, the displayed image slices are 2D projected renderings such as maximum intensity projections (MIPs), minimum intensity projections (MinIPs), mean intensity projections (meanIPs), or the like, wherein pixels of 3D data are projected to a 2D plane based on pixel intensity (maximum intensity, minimum intensity, mean intensity, etc.). The GUI may be displayed on a display device (e.g., display device 236 of FIG. 2) and may include one or more selectable elements and/or tools through which the user may interact with the images, annotate the images, or perform other actions. For example, the GUI may include a segmentation element that when selected via user input launches a segmentation tool menu. The 3D multi-volume imaging dataset may comprise images obtained from one or more orientations and therefore images may be displayed in one of various views, e.g., an axial view, sagittal view, coronal view, and/or the like. In some examples, each of the one or more images displayed may be displayed from the same view.

Further, the plurality of images may additionally comprise images not displayed within the GUI as well as those one or more images displayed. The GUI may, in some examples, include a menu through which the user may select which of the plurality of images are displayed. For example, a 3D multi-parametric imaging dataset may include volumes from a T1 sequence, a T1CE sequence, a FLAIR sequence, a DWI sequence, and a T2 weighted sequence. The user may select, for example, the T1 sequence, the FLAIR sequence, and the T2 weighted sequence to be displayed within the GUI. The DWI sequence and the T1CE sequence may be stored in transitory and/or non-transitory memory and may be displayed within the GUI upon user selection via the menu. In other examples, each of the plurality of images of the 3D multi-volume imaging dataset may be displayed within the GUI.

At 306, the method 300 includes receiving user input(s) of position(s) of a user cursor within a first image slice of the displayed image slices corresponding to the one or more images. The first image slice may be of a first image volume. The user cursor may be adjustable via user inputs (e.g., movement of a user input device such as a mouse) and the position of the user cursor may be determined via user input (e.g., a mouse click). The position of the user cursor may be determined relative to the displayed image/2D slice. In some examples, a coordinate system may be predefined for the 3D multi-volume imaging dataset and the volumes thereof and, therefore, the coordinate system may be the same for each of the volumes. The position of the user cursor may therefore be known within the first image slice and because the coordinate system is the same for each of the volumes, the position of the user cursor may be transposed to the other of the plurality of images. In some examples, more than one position of the user cursor may be determined, for example as the user moves the user cursor from an initial position around a region of interest. One or more positions may be defined along a line, the first position being a position the user cursor is in when an initial user input is received (e.g., a mouse click) and one or more second positions being defined (e.g., by dragging with the mouse clicked) until the initial user input is released (e.g., releasing the mouse click). The user inputs defining the position of the user cursor may be annotation inputs.

At 308, method 300 includes computing a segmentation contour for each of the displayed image slices based on the position(s) of the user cursor. As will be described in greater detail with respect to FIG. 4, for each position of the user cursor, a position of a point, e.g., contour point position, may be determined within each of the displayed image slices at the same time. The computed point may be one of a plurality of points of the segmentation contour. Thus, for a given set of user cursor positions inputted to the first image slice, a segmentation contour may be defined for each of the plurality of images of the 3D multi-volume imaging dataset.

Determination of contour points from the user cursor position may be performed in real-time or near real-time (e.g., without intentional delay), whereby as annotation inputs are received defining user cursor positions, contour points are added to respective image slices in real-time. In this way, the user may be able to efficiently visualize the contour points as they are determined. Additionally, processing efficiency may be increased by the real-time nature of the annotation. For example, since a single annotation input may generate multiple contour points in real-time, processing time and power may be reduced as repeated annotations are mitigated and determination of contour points may be performed based on a single acquisition of a position of the user cursor. In this way, annotation and segmentation of data of multiple volumes may be more efficiently performed as determination of contour points and generation of corresponding segmentation contours need not be completed based on independent annotation inputs to each respective volume.

In this way, an annotation input defining a user cursor position to a single image slice may result in outputted contour points for a plurality of images (e.g., displayed 2D slices), therefore reducing time spent by the user in annotating the images and in processing power as the number of user inputs is reduced. Further, computing segmentation contours for each of a plurality of images of the same region of interest increases the amount of data available when annotating and segmenting, therefore increasing accuracy of a resultant segmentation as the region of interest may be visualized and analyzed from various sequences that show internal anatomy differently.

At 310, method 300 includes displaying respective segmentation contours as overlays on corresponding image slices. Each of the segmentation contours computed at 308 may differ from one another as each position of the user cursor corresponds to independently computed contour point positions within each of the image slices. As an example, a first segmentation contour computed for the first 2D slice may be displayed as an overlay on the displayed first image slice within the GUI. A second segmentation contour computed for a second 2D slice may be displayed as an overlay on the displayed second image slice within the GUI. In some examples, the first segmentation contour may be displayed with a first color and the second segmentation contour may be displayed with a second, different color. In other examples, the first and second segmentation contours may be displayed with the same color in the GUI.

In some examples, each of the respective segmentation contours may be editable. For example, via a user input such as a mouse click, a position of point of a segmentation contour may be altered without having to repeat computation of the point, thereby reducing processing power as repeated computations are avoided.

At 312, method 300 optionally includes displaying all the computed contours as overlays on each of the image slices. In some examples, all the computed contours may be displayed as overlays on each of the image slices such that the user may visualize the contours in comparison to each of the one or more images. In this way, the user may be able to determine which of the computed contours best approximates a shape of the region of interest ("best" being a subjective determination by the user when comparing segmentation contours). As noted above, each of the displayed image slices may belong to a set of image slices for a particular coordinate and a selected contour may be defined for the set of image slices for that particular coordinate. In this way, a plurality of contours may be selected, each for a different coordinate/set of image slices, as will be described with respect to FIG. 5.

At 314, method 300 includes receiving user input selecting one of the overlaid contours. In some examples, each of the overlaid contours may be assigned a number to allow for differentiation thereof. Each of the overlaid contours may be selectable elements that when selected via user input, such as a mouse click or keyboard touch (e.g., keyboard touch corresponding to an assigned number), indicates that the selected segmentation contour for the one or more displayed images (e.g., of the displayed particular set of image slices) are to be saved. Alternatively or additionally, all of the segmentation contours may be selected.

At 316, method 300 includes saving the selected segmentation contour to memory. In response to user selection of the selected segmentation contour, the selected segmentation contour may be saved to memory to be accessed and/or used at a later date. For example, the selected segmentation contour may be used to interpolate a 3D segmentation mask, as will be further described with respect to FIG. 5. In this way, the 3D segmentation mask may be generated at least in part on the selected segmentation contour. Steps of the method 300 may be performed, for example from 304 through 316, for two or more sets of image slices of the volumes in order to define multiple segmentation contours for each volume (e.g., each at a different coordinate) and a selected segmentation contour may be selected for each respective coordinate. The plurality of selected contours may then be used to form a segmentation mask.

Turning now to FIG. 4, a flowchart illustrating an example method 400 for determining contour point positions and computing segmentation contours is shown. The method 400 will be described with relation to the systems depicted in FIGS. 1-2, but it should be understood that similar methods may be used with other systems without departing from the scope of this disclosure. The method 400 may be carried out via instructions stored in non-transitory memory of one or more computing devices. In some examples, the method 400 may be carried out by a computing device (e.g., the computing device that comprises the processor 202 of the image processing system 200 of FIG. 2) as well as a set of remote servers, also referred to herein as a cloud computing system, in communication with the computing device. The computing device may be in communication with an imaging archive (e.g., imaging archive 238). The method 400 may be an example method implemented as part of method 300 of FIG. 3, specifically at 308. It should be understood that other methods of computing segmentation contours and determining contour point positions are possible without departing from the scope of this disclosure.

At 402, method 400 includes obtaining a plurality of images of a 3D multi-volume imaging dataset from the imaging archive. The multi-volume imaging dataset may be acquired via an imaging system (e.g., MRI system 10 of FIG. 1) configured for acquiring multi-volume data, such as multi-parametric imaging data and/or multi-phase imaging data. In some examples, the multi-volume imaging dataset that is to be segmented may be selected via user input. For example, a user may select a desired multi-volume imaging dataset to be segmented and may request, via user input, that the selected 3D multi-volume imaging dataset be segmented (e.g., by selecting a segmentation tab, tool, or the like). The 3D multi-volume imaging dataset may comprise a plurality of registered image volumes, each image volume from a different imaging sequence or phase of the same field of view. As is described above, the plurality of image volumes may be registered to each other. In some examples, each of the plurality of registered image volumes may be partitioned into a plurality of image slices. In some examples, the plurality of image slices for each of the plurality of registered image volumes may have the same set of image slice coordinates (e.g., slice positions for a given axis). The obtained plurality of images may be a plurality of registered image volumes.

At 404, method 400 includes displaying an image slice of one or more of the plurality of registered image volumes in a GUI. The GUI may be displayed on a display device (e.g., display device 236 of FIG. 2) and may include one or more selectable elements and/or tools through which the user may interact with the images, annotate the images, or perform other actions. For example, the GUI may include a segmentation element that when selected via user input launches a segmentation tool menu. The 3D multi-volume imaging dataset may comprise images obtained from one or more orientations (e.g., axes) and therefore images may be displayed in one of various views, e.g., an axial view, sagittal view, coronal view, and/or the like. In some examples, each of the one or more images displayed may be displayed from the same view.

Further, as is described with respect to FIG. 3, the plurality of images may comprise images not displayed within the GUI. The GUI may, in some examples, include a menu through which the user may select which of the plurality of images are displayed. In other examples, each of the plurality of images of the 3D multi-volume imaging dataset may be displayed within the GUI.

At 406, method 400 includes receiving user input of a position of a user cursor within a first image slice of the displayed image slices. The first image slice may correspond to a first imaging volume. The user cursor may be adjustable via user inputs (e.g., movement of a user input device such as a mouse) and the position of the user cursor may be selected via user input. The position of the user cursor may be determined relative to the displayed image slice. In some examples, a coordinate system may be predefined for the 3D multi-volume imaging dataset and the volumes thereof and therefore, the coordinate system may be the same for each of the volumes. The position of the user cursor may therefore be known within the first image slice and because the coordinate system is the same for each of the volumes, the position of the user cursor may be transposed to the other of the plurality of images.

At 408, method 400 includes defining a geodesic propagation around the position of the user cursor for each of two or more image slices corresponding to two or more image volumes. The geodesic propagation may be a circle, wherein a radius of the circle is dependent upon tonal distributions within the propagation area, as noted at 410. For example, a larger propagation area may be defined for a smaller tonal distribution range (e.g., pixel intensities are relatively the same) and a smaller propagation area is defined for a larger tonal distribution range. The geodesic propagation may define the area of influence of the user cursor, whereby pixels within that propagation area are considered for gradients, edges, and/or contour points.

At 412, method 400 includes determining gradients within the geodesic propagation area for each respective image slice. As noted, the geodesic propagation area around the position of the user cursor may define an influence zone. The determined gradients may be changes in pixel intensity between adjacent pixels determined to correlate to an edge of a region of interest, for example as determined by the processor 202 based on instructions stored in the flat zone characterization module 208 of FIG. 2. In some examples, the area within the geodesic propagation may be considered a flat zone when all the pixel intensities therewithin are the same or relatively the same (e.g., ±a specified amount of noise) and no gradients are detected. If one or more gradients are detected, the edge of the region of interest may be detected. Edge detection may define a designated area around the user cursor. The designated area may combine the geodesic propagation area with detected edges and the designated area may therefore not be a circle.

At 414, method 400 includes determining a contour point based on the position of the user cursor and the determined gradient points for each respective image slice. In some examples, a circularity criterion may be applied, as noted at 416. The circularity criterion provides an indication of how round a contour to which the contour point belongs is, where a circularity values range from 0 to 1, with values closer to 0 being less round and values closer to 1 being more round. In some examples, the contour point position may be the closest edge position to the position of the user cursor, as noted at 418. In this way, the contour point may lie along a ray of the user cursor. As such, if two user cursors lie along the same ray, the same contour point may be proposed for both of the two user cursor position for a give image slice.

In some examples, the position of the contour point or a given image slice may be stabilized based on a prior contour point position of the given image slice, as noted at 420. In cases in which the contour point is the first contour point of a segmentation contour, stabilization may not be performed. In cases in which the contour point is not the first contour point, stabilization may be performed. A method for stabilization may comprise a low pass filter wherein the contour point is equal to a previous contour point plus a defined displacement, the defined displacement being the difference between the contour point and the previous contour point.

At 422, method 400 includes determining whether additional contour points are needed to generate respective segmentation contours. Each segmentation contour may be generated based on a plurality of contour point positions. As described with respect to FIG. 3, user input, such as a left mouse click and drag, may indicate an initial user cursor position and one or more subsequent user cursor positions. A second user input, such as a release of a mouse click, may indicate that no additional contour points are to be added to the segmentation contour (e.g., the segmentation contour is complete). In some examples, the segmentation contour may be considered complete when a final contour point approximates an initial contour point.

If additional contour points are to be added to generate the segmentation contour, method 400 returns to 406 to receive user input of a position of the user cursor within the first image slice. The user input may be a mouse click or a drag of the mouse, as previously described. New contour points may be added as the cursor is moved when the determined contour point is different from a previously determined contour point. If no additional contour points are to be added, method 400 proceeds to 424.

Contour points may be added in real-time (e.g., without intentional delay) as annotation inputs are added to the first image slice. Within the GUI, this may be demonstrated by a contour point being added at or near the same time as a corresponding annotation input is inputted. For example, as the user drags the user cursor, contour points within each respective image slice may be added and displayed for viewing. In this way, efficiency and accuracy may be increased as real-time interpretation may be done by the user. Further, processing may be more efficient due to the real-time nature of the annotation.

At 424, method 400 includes generating the segmentation contour based on the plurality of contour points. In some examples, interpolation may be performed between adjacent contour points to generate a contour line therebetween. For example, a plurality of contour points that approximates a circle may generate a circular segmentation contour via interpolation between points. As the contour points approximate an edge of the region of interest, the segmentation contour may approximate a shape of the region of interest. Following 424, method 400 ends.

Turning now to FIG. 5, a flowchart illustrating an example method 500 for generating a 3D segmentation mask from a plurality of 2D segmentation contours is shown. The method 500 will be described with relation to the systems depicted in FIGS. 1-2, but it should be understood that similar methods may be used with other systems without departing from the scope of this disclosure. The method 500 may be carried out via instructions stored in non-transitory memory of one or more computing devices. In some examples, the method 500 may be carried out by a computing device (e.g., the computing device that comprises the processor 202 of the image processing system 200 of FIG. 2) as well as a set of remote servers, also referred to herein as a cloud computing system, in communication with the computing device. The computing device may be in communication with an imaging archive (e.g., imaging archive 238). Method 500 may be performed in conjunction with methods 300 and 400.

At 502, method 500 includes obtaining a plurality of images of a 3D multi-volume imaging dataset from an imaging archive (e.g., imaging archive 238 of FIG. 2). As described with respect to FIG. 3, each of the plurality of images may be a 3D volumetric image (e.g., an image volume) and may comprise a plurality of image slices, as noted at 504. The plurality of images may comprise 3D volumetric images of different sequences, phases, and/or parameters, as previously described. Further, also as described with respect to method 300, in some examples, the 3D multi-volume imaging dataset that is to be segmented may be selected via user input.

At 506, method 500 includes, for a selected first set of image slices, generating a plurality of first segmentation contours, one contour of the plurality of first segmentation contours corresponding to each of first set of image slices. Each of the image slices of the first set of image slices may correspond to a respective image volume of the plurality of images. The plurality of first segmentation contours may correspond to a region of interest imaged by the imaging system. The selected first set of image slices may be selected via user input, such as scrolling through the plurality of image slices to select one of the plurality of 2D slices. As is described with respect to FIGS. 3 and 4, user cursor positions may be determined within one of the plurality of images and may be used to compute corresponding contour point positions for each of the plurality of images for the selected first set of image slices. For example, computing the corresponding contour point position may include definition of a geodesic propagation, determination of one or more gradients, wherein the one or more gradients correlate to an edge of the region of interest, and determination of a point at the gradient edge that is closest to the user cursor position. A plurality of user cursor positions inputted to one of the first set of image slices and corresponding respective pluralities of contour points may define a first segmentation contour for each of the selected first set of image slices. As described previously, each of the plurality of segmentation contours may differ from each other as the computation of contour point positions is performed independently for each of the image slices.

At 508, method 500 includes receiving user input selecting a first selected contour of the plurality of first segmentation contours. As described with respect to FIG. 3, user input such as a mouse click or keyboard touch, may select the first selected contour for the selected first set of image slices. The first selected contour may be saved to memory for the corresponding selected first set of image slices.

At 510, method 500 includes, for one or more selected second sets of image slices, generating respective pluralities of contours. In some examples, the image slices of the one or more selected second sets of image slices may correspond to the same image volumes as the first set of image slices. The one or more selected second sets of image slices may be selected similar to as the selected first set of image slices. For example, following selection of the first selected contour, user input, such as scrolling through the plurality of image slices, may select a second set of image slices. User cursor positions may be determined within one of the image slices of each of the one or more second sets of image slices and may be used to compute corresponding contour point positions for each of image slices for respective second sets of image slices. Computation of contour point positions and corresponding segmentation contours may be as described at 504. For each of the one or more selected second sets of image slices, a plurality of second contours may be generated. Each of the plurality of second contours may be specific to one of the plurality of images of the 3D multivolume imaging dataset.

Similar to as described with respect to FIG. 3, each of the computed contours may be displayed as overlays on respective image slices. Further, each of the computed and displayed contours may be adjustable to change position of one or more contour points if so desired by the user. For example, via user input, a point of a specified contour may be adjusted from an initial position to a second position, therefore altering the specified contour.

At 512, method 500 includes receiving user inputs selecting a contour of each of the plurality of second contours to define a selected contour for each of the one or more second sets of image slices. Selection of the first and the one or more selected second contours may define a set of selected contours for the 3D multi-volume imaging dataset. In some examples, the set of selected contours may include a selected contour for each set of image slices of the 3D multi-volume imaging dataset. In other examples, the set of selected contours may include a selected contour for each of a subset of the sets of image slices of the 3D multi-volume imaging dataset.

At 514, method 500 includes interpolating between the selected contours to generate a 3D segmentation mask. As noted, each of the selected contours may be 2D. In some examples, each of the selected contours may have a known coordinate, for example, in an axial view each slice may have a known z-coordinate. The plurality of selected contours may comprise a stack of 2D contours each with a different coordinate along a particular axis. Interpolation, in this context, may comprise estimating point positions between the selected contours to define a 3D shape from a plurality of 2D contours. The defined 3D shape may approximate the region of interest to be segmented.

At 516, method 500 includes generating a 3D segmentation mask based on the interpolation. The 3D shape that is defined by the interpolation may define the 3D segmentation mask of the region of interest. As an example of a method of generating the 3D segmentation mask, data points of the interpolated 2D segmentation contours may be projected into or mapped to the 3D space in which the 3D multivolume imaging dataset was originally obtained in. The resulting 3D segmentation mask may define pixels included in and pixels excluded from the region of interest. The 3D segmentation mask may be saved to memory of the computing device and may be accessible for later use. For example, other users may access the 3D segmentation mask to view the 3D segmentation mask for diagnostic, evaluation, or other purposes. The 3D segmentation mask may incorporate data of multiple volumetric images of the region of interest, as herein described, and may therefore provide a 3D segmentation mask with a more accurate representation of the region of interest.

Processing demands for segmentation may therefore be reduced by allowing for segmentation of 2D slices and interpolating to a 3D mask rather than segmenting 3D data on its own. Segmentation of 3D data on its own is inefficient with regards to time as well as processing power. Segmenting one or more 2D image slices and then interpolating back to the 3D space may be more time efficient and may reduce the processing power.

In some examples, a representation of the 3D segmentation mask may be displayed on the display device, either as an overlay on one or more images, or in a separate window. The representation of the 3D segmentation mask may demonstrate the shape of the region of interest and in some examples may be interactive such that the user, via user inputs, may change an orientation, rotate, move, etc. the representation in order to visualize different angles.

Turning now to FIG. 6, example images of a first multivolume imaging dataset of a patient are shown. The first multi-volume imaging dataset may be a multi-parametric imaging dataset that includes a plurality of registered image volumes from various imaging sequences acquired of the same field of view. For example, the first multi-volume imaging dataset may be of a multi-parametric MRI scan of a brain, as shown in FIG. 6.

The first multi-volume imaging dataset may include a first image 602 of a first volume, a second image 604 of a second volume, and a third image 606 of a third volume. The first, second, and third volumes may include a plurality of images, or 2D slices, thereof. The first, second, and third images 602, 604, and 606 may include data of the same anatomy of the patient. For example, a region of interest 610, which may be a lesion, a tumor, a region of an organ, or other feature, may be present in each of the first, second, and third volumes. In some examples, the first volume may be of a T1 sequence, the second volume may be of a T1CE sequence, and the third volume may be of a FLAIR sequence. Additional sequences may be included in the first multi-volume imaging dataset not shown here. Each of the sequences of the first multi-volume imaging dataset may be acquired by an imaging system during a single scan acquisition. Therefore, the region of interest 610 may be imaged through each of the sequences during the same period of time.

Each of the sequences of the first multi-volume imaging dataset may focus, highlight, or otherwise show different parts of the anatomy that is imaged. For example, the T1CE sequence may show areas of enhancement more than the T1 sequence. In this way, the region of interest 610 may be viewed with multiple parameters, providing increased information about the region of interest which may be used to more accurately segment the region of interest from surrounding anatomy.

FIG. 7 similarly shows examples of images of a second multi-volume imaging dataset, including a first image 702 of a first volume, a second image 704 of a second volume, a third image 706 of a third volume, and a fourth image 708 of a fourth volume. The second multi-volume imaging dataset, in some examples, may be a multi-phase imaging dataset such as a multi-phase CT scan of a liver, as shown in FIG. 7.

Similar to the first multi-volume imaging dataset, the volumes of the second multi-volume imaging dataset may include a plurality of images and the first, second, third, and fourth images 702, 704, 706, and 708 may each be one of respective pluralities of images. As an example, the first volume may be a first phase, such as a non-contrasted phase, the second volume may be of a second phase, such as an arterial phase, the third volume may be of a third phase, such as a portal venous phase, and the fourth volume may be of a fourth phase, such as a delayed phase. The phases may be obtained at varying times during scan acquisition, in some examples as a contrast agent travels through vasculature. Also similar to the first multi-volume imaging dataset, each of the volumes of the second multi-volume imaging dataset may include data of the same region of interest, such as region of interest 710. The region of interest 710 may appear differently in each of the volumes due to the different phases. In this way, additional information about the region of interest 710 may be provided, and therefore segmentation of the region of interest 710 may be more accurate.

Images of both the first and second multi-volume imaging datasets may be acquired by an imaging system, stored in an imaging archive, and displayed within a GUI. Via user interaction with the images displayed within the GUI annotating the images, a region of interest, such as regions of interest 610 and/or 710, may be segmented, via methods as described with respect to FIGS. 3-5.

Turning now to FIG. 8, an example GUI 800 is shown. The GUI 800 may be displayed on a display device, such as display device 236 of FIG. 2, in communication with an image processing system, such as image processing system 200 of FIG. 2. The GUI 800 may display one or more images of a multi-volume imaging dataset of a patient acquired by an imaging system and stored within an imaging archive, such as imaging archive 238, which is in communication with the image processing system.

As noted, the GUI 800 may display one or more images of the multi-volume imaging dataset. For example, the GUI 800 may display a first image 802, a second image 804, and a third image 806. In some examples, the first, second, and third image 802, 804, and 806 may each belong to different volumes of the multi-volume imaging dataset. For example, the different volumes may be from different sequences or from different phases. As is explained previously, a region of interest 810 may be imaged in each of the volumes. In some examples, the GUI 800 may display one image slice (e.g., 2D slice) of a respective image volume at a time.

In some examples, the GUI 800 may comprise a menu 820 for available sequences or phases of the multi-volume imaging dataset. Each of the available sequences may be displayed as selectable elements in a list, such as sequence 822. Two or more of the listed sequences may be selected at one time. When selected, images of volumes corresponding the selected two or more sequences (e.g., a slice of a corresponding image volume) may be displayed within the GUI 800.

The GUI 800 may further comprise a plurality of tool icons 824 that when selected via user input, launch a corresponding tool, such as a ruler tool, a brightness adjustment tool, a segmentation tool, and the like through which a user may interact with the one or more images. A user cursor 812 may be moveable via user inputs with a user input device, such as a mouse, in communication with the display device. When the segmentation tool is selected, a first type of user input, such as a mouse click, may indicate a position of the user cursor 812, as is described with respect to the method 400. In some examples, the position of the user cursor 812 may determine positions of a contour point (e.g., a point of a segmentation contour) within each of the one or more displayed images, as is described with respect to FIG. 4. In other examples, the position of the user cursor 812 may determine positions of a contour point within each of the images of the multi-volume imaging dataset, even those images not displayed within the GUI 800 at the time of the user input.

Turning now to FIG. 9, the GUI 800 of FIG. 8 is shown following determination of the position of a plurality of contour points. Each of the plurality of contour points may be displayed in a corresponding position as an overlay within a respective image. For example, a first contour point 900 may be displayed within the first image 802, a second contour point 902 may be displayed within the second image 804, and a third contour point 904 may be displayed within the third image 806. Each of the first, second, and third contour points 900, 902, and 904 may be displayed at the same time. Positions of the first, second, and third contour points 900, 902, and 904 may be independently determined based on the position of the user cursor 812 and flat zone characterization, tonal distributions, and gradients of the corresponding images, as is described with respect to method 400. In some examples, positions of additional contour points for images not displayed within the GUI 800 at the time the user input is received may also be determined based on the position of the user cursor 812.

Turning now to FIGS. 10 and 11, a zoomed in view 1000 of a portion of the first image 802 of GUI 800 and a zoomed in view 1002 of a portion of the second image 804 of GUI 800 are shown. As is described in detail with respect to method 400, the user cursor 812 may be positioned within a specified distance of an edge of the region of interest 810 such that when generating a geodesic propagation and determining gradients therewithin, the gradients may be detected within the propagation area. Rays may be defined to determine a closest point of the edge of the region of interest 810 and the user cursor 812. The determined edge of the region of interest 810 may be based on tonal distributions and detected gradients and as such may differ for each of the first image 802 and the second image 804. Therefore, a position of the first contour point 900 and the second contour point 902 may differ.

Because of the rays that are defined during determination of contour points, positions of user cursors that are within the same ray may generate a single contour point in each image. For example, as shown in FIG. 11, a first user cursor position 1104 may result a first contour point 1108. A second user cursor position 1106, when in the same ray as the first user cursor position 1104 with respect to an edge of the region of interest 810, may also result in the first contour point 1108, the same as the first user cursor position 1104.

Turning now to FIG. 12, an example of a plurality of segmentation contours are shown. In some examples, the plurality of segmentation contours may be displayed as overlays within corresponding images displayed within a GUI. In other examples, the plurality of segmentation contours may be displayed as overlays within each of a plurality of images displayed within the GUI.

As an example, a GUI may display a first image 1200, a second image 1202, a third image 1204, and a fourth image 1206. Each of the first, second, third, and fourth images 1200, 1202, 1204, and 1206 may belong to different image volumes of a multi-volume imaging dataset. In some examples, each of the first, second, third, and fourth images 1200, 1202, 1204, and 1206 may include a region of interest 1250. Each of the plurality of segmentation contours may approximate a shape of the region of interest 1250. The plurality of segmentation contours may include a first segmentation contour 1210 corresponding to the first image 1200, a second segmentation contour 1212 corresponding to the second image 1202, a third segmentation contour 1214 corresponding to the third image 1204, and a fourth segmentation contour 1216 corresponding to the fourth image 1206.

As shown in FIG. 12, the plurality of segmentation contours may be displayed as overlays within respective images in various stages of completeness. For example, in a first row 1230, the plurality of segmentation contours are displayed when incomplete, as would be the case while a user is actively annotating. For example, the plurality of segmentation contours may be updated dynamically as user inputs are added to repeatedly add points to the segmentation contour, as described with respect to FIG. 4. When displayed when incomplete, each of the plurality of segmentation contours may include a current contour point, such as current contour point 1240 of the first segmentation contour 1210. As shown in a second row 1232, the plurality of segmentation contours may be displayed once annotation is complete. In some examples, completion of annotation may be reached when a current contour point equals or approximates an initial contour point.

In some examples, as is described with respect to FIGS. 3-5, each of the plurality of segmentation contours may be independently adjustable. For example, selection of a region or a point within a segmentation contour may be moved. In this way, a given segmentation contour may be adjusted to better approximate the region of interest.

As shown in a third row 1234, the plurality of segmentation contours may all be displayed within each of the plurality of images. In some examples, each of the plurality of segmentation contours, as shown in FIG. 12, may be colored to differentiate therebetween. For example, the first segmentation contour 1210 may be orange, the second segmentation contour 1212 may be gray, the third segmentation contour 1214 may be blue, and the fourth segmentation contour 1216 may be yellow. In this way the different segmentation contours may be differentiated from one another when all displayed in as overlays in a single image.

Displaying all the segmentation contours within each of the plurality of displayed images may allow the user to view the segmentation contours compared to the region of interest. In this way, the user may determine which of the plurality of segmentation contours best approximates the region of interest as is visualized in each of the plurality of images. Each of the plurality of segmentation contours may be selectable via one or more types of user inputs (e.g. a mouse click, a key touch, etc.), as previously described, such that the user may select one of the plurality of images. With annotation of multi-volume imaging, such as multi-parametric and/or multi-phase imaging, the region of interest may be seen as imaged from a variety of sequences or phases and segmentation contours may be generated for each of the volumes, for example at a particular slice. The plurality of segmentation contours may allow for increased accuracy of annotation and segmentation as a more robust approximation of the region of interest may be determined.

Turning now to FIG. 13, an illustration of a geodesic propagation and a corresponding defined area around a user cursor is shown. As described with respect to FIG. 4, when determining a contour point position from a user cursor position, a geodesic propagation 1302 is generated around a user cursor 1308. The geodesic propagation 1302 may be circular. The geodesic propagation 1302 is constrained by a radius 1320 which is dependent upon tonal distributions, as previously described. When pixels (or voxels) within the geodesic propagation 1302 have the same intensity, the area of the geodesic propagation may be considered a flat zone 1306.

When the user cursor 1308 is within range of an edge of a region with varying pixel intensities, which in some examples may be a region of interest of a medical image, one or more gradients may be detected. The user cursor 1308 may be within range of the edge of the region of interest when gradients are detected within the geodesic propagation 1302. Gradients may define an edge 1322 which results in a designated area 1304 around the user cursor 1308 not being circular. A closest point 1310 of the edge 1322 to the user cursor 1308 may be a contour point for a corresponding segmentation contour.

Generation of geodesic propagations and detection of gradients may be performed independently for each volume of a 3D multi-volume imaging dataset comprising a plurality of image volumes registered. For example, 2D slices may be displayed each belonging to one of a plurality of registered image volumes and based on the geodesic propagation and detected gradients, a contour point may be defined for each 2D slice individually, as described previously. In this way, a single user cursor position, inputted by the user during an annotation, may define points of a segmentation contour for each volume.

Varying tonal distributions and resultant radii of designated areas around a user cursor are shown with respect to FIGS. 14 and 15. In FIG. 14, a user cursor 1404 is overlaid on a medical image 1402 displayed within a GUI 1400 in a first position. In the first position, the user cursor 1404 is positioned overlying a region 1406 of a brain. The region 1406 may have a defined tonal distribution and/or tonal distribution range thereof. The user cursor 1404 may be within a distance of a region of interest 1408, where the distance is less than a radius of a geodesic propagation around the user cursor 1404. The radius of the geodesic propagation area may be dependent upon the defined tonal distribution of the region 1406. A designated area 1410 around the user cursor 1404, displayed as an overlay within the GUI 1400, may take into account detected gradients, for example those associated with an edge of the region of interest 1408, and may therefore not be a circle, as is described with respect to FIG. 13.

In FIG. 15 a user cursor 1504 is overlaid on a medical image 1502 displayed within a GUI 1500 in a second position. The user cursor 1504 may be the user cursor 1404, the medical image 1502 may be the medical image 1402, and the GUI 1,500 may be the GUI 1400, in some examples. In the second position, the user cursor 1504 may be positioned overlying a background 1506, as opposed to the user cursor 1404 which is positioned overlying the region 1406 of the brain of the medical image. The background 1506 may comprise pixels of all the same pixel intensity. A radius 1512 of a geodesic propagation around the user cursor 1504 may be greater than the radius of the geodesic propagation area around the user cursor 1404 because a defined tonal distribution of the background 1506 is less than the tonal distribution of the region 1406. Smaller tonal distributions may result in larger radii of potential designated areas. Similar to FIG. 14, an edge 1508 (e.g., an edge of the brain) may be within the geodesic propagation area as a distance between the edge 1508 and the user cursor 1504 is less than the radius of the geodesic propagation area. A designated area 1510, displayed as an overlay within the GUI 1500, may not be a circle due to the detected edge 1508, as described with respect to FIG. 4.

The technical effect of the methods and systems provided herein is that multi-volume imaging data may be annotated to more accurately segment a region of interest of the multi-volume imaging data. Annotation may comprise user input to one of a plurality of volumes (e.g., to define position of a user cursor) and generation of contour points and segmentation contours for each of the plurality of volumes based on the position of the user cursor. Determination of contour points may be based on flat zone characterization and determining a closest point of a gradient/detected edge to the position of the user cursor. Multiple options for a selected segmentation contour may allow for a more accurate segmentation.

Further, generating segmentation contours for each of the volumes of the multi-volume imaging data via user input to one volume (e.g., an image of a volume), processing demands for the computing device may be reduced as the amount of user inputs may be reduced. For example, when generating segmentation contours for a set of image slices, an input to a single image slice are used to determine a corresponding contour point for each of two or more of the image slices. The algorithm to define the corresponding contour point may be applied at the same time to each of the two or more image slices based on the input to the single image slice. Therefore, application of inputs to each individual image slice and separated completions of the algorithm, which would result in increased processing power and time spent, is avoided and overall a lower amount of processing is demanded by the computing system.

Further, annotation and generation of segmentation contours as herein described may be performed in real-time whereby contour points are added to respective images in real-time as annotation inputs (e.g., mouse clicks or drags) are added to an image. In this way, the methods and systems herein may reduce time spent by the user in annotation and segmentation as well as increasing processing efficiency.

The disclosure also provides support for a method, comprising: obtaining three-dimensional (3D) multi-volume imaging data, the 3D multi-volume imaging data comprising a plurality of registered image volumes, determining one or more positions of a user cursor within a first image of a first image volume of the plurality of registered image volumes, determining a contour point position corresponding to each of the one or more positions of the user cursor for two or more of the plurality of registered image volumes, generating two or more segmentation contours corresponding to the two or more of the plurality of registered image volumes, determining, via user input to a display device, a selected segmentation contour of the two or more segmentation contours, generating a three-dimensional (3D) segmentation mask based at least in part on the selected segmentation contour, and saving the 3D segmentation mask to memory. In a first example of the method, the plurality of registered image volumes are each partitioned into a plurality of image slices and the first image is a first image slice of the first image volume. In a second example of the method, optionally including the first example, the contour point is one of a plurality of points of a corresponding segmentation contour. In a third example of the method, optionally including one or both of the first and second examples, the 3D multi-volume imaging data is acquired by an imaging system configured to acquire one of multi-parametric and multi-phase imaging data. In a fourth example of the method, optionally including one or more or each of the first through third examples, a representation of the segmentation mask is displayed to the user via the display device. In a fifth example of the method, optionally including one or more or each of the first through fourth examples, each of the plurality of registered image volumes includes data of a region of interest and the segmentation mask corresponds to the region of interest. In a sixth example of the method, optionally including one or more or each of the first through fifth examples, determining each of the two or more segmentation contours comprises, for each of the one or more positions of the user cursor: defining a geodesic propagation around a position of the user cursor, wherein the position of the user cursor is within a distance of a region of interest of the first image, the distance being less than a radius of the geodesic propagation, detecting one or more gradients within the geodesic propagation, wherein the one or more gradients correlate to an edge of the region of interest, defining the edge of the region of interest based on the one or more gradients, and determining a point of the edge that is closest to the position of the user cursor, wherein the point is one of two or more points of a corresponding segmentation contour. In a seventh example of the method, optionally including one or more or each of the first through sixth examples when the geodesic propagation is 2D, the geodesic propagation is a circle and the radius of the geodesic propagation depends on tonal distributions within the geodesic propagation. In a eighth example of the method, optionally including one or more or each of the first through seventh examples, generating the segmentation mask comprises interpolating between two or more selected segmentation contours.

The disclosure also provides support for a system, comprising: an imaging system configured to acquire three-dimensional (3D) multi-volume imaging data, and a computing device communicably coupled to the imaging system, the computing device configured with instructions stored in non-transitory memory executable by a processor that, when executed, cause the processor to: obtain a 3D multi-volume imaging dataset from an imaging archive, wherein the 3D multi-volume imaging dataset comprises a plurality of registered image volumes each comprising a plurality of image slices, display an image slice of a first set of image slices of two or more image volumes of the plurality of registered image volumes within a graphical user interface (GUI) of a display device communicably coupled to the computing device, determine two or more positions of a user cursor within a first image slice of a first image volume in response to user input, determine contour points within two or more image slices corresponding to two or more of the plurality of registered image volumes based on the two or more positions of the user cursor within the first image slice, generate two or more segmentation contours, wherein each of the two or more segmentation contours corresponds to one of the two or more image slices and comprise respective pluralities of contour points, select, in response to user input, a selected segmentation contour of the two or more segmentation contours, generate, based on the selected contour, a 3D segmentation mask, and save the 3D segmentation mask to non-transitory memory. In a first example of the system, each of the plurality of registered image volumes corresponds to one of a different imaging sequence and a different imaging phase. In a second example of the system, optionally including the first example, each of the two or more segmentation contours is displayed on the display device with a different color, wherein a first segmentation color is displayed with a first color and a second segmentation contour is displayed with a second, different color. In a third example of the system, optionally including one or both of the first and second examples, two or more positions of the user cursor are known within each of the two or more image slices. In a fourth example of the system, optionally including one or more or each of the first through third examples, the computing device is further configured with instructions stored in non-transitory memory that when executed, cause the processor to determine two or more second segmentation contours corresponding to a second set of image slices. In a fifth example of the system, optionally including one or more or each of the first through fourth examples, the computing device is further configured with instructions stored in non-transitory memory that when executed, cause the processor to select, in response to user input, a second selected segmentation contour of the two or more second segmentation contours.

The disclosure also provides support for a method, comprising: determining a position of a user cursor within a first image of a first image volume of a plurality of image volumes of a 3D multi-volume imaging dataset, generating a geodesic propagation around the position of the user cursor within two or more images of two or more corresponding image volumes of the plurality of image volumes, determining one or more gradients within the geodesic propagation of each of the two or more images, defining an edge of a region of interest within the geodesic propagation of each of the two or more images based on the one or more gradients, determining a point of the edge closest to the position of the user cursor within each of the two or more images, and saving the point as one of a plurality of points of a segmentation contour for each of the two or more images. In a first example of the method, the method further comprises: generating a segmentation mask based at least in part on a selected segmentation contour of one of the two or more images and displaying a representation of the segmentation mask. In a second example of the method, optionally including the first example, a prior point of a respective segmentation contour stabilizes the point. In a third example of the method, optionally including one or both of the first and second examples, the geodesic propagation is constrained to a radius depending on tonal distributions within the geodesic propagation. In a fourth example of the method, optionally including one or more or each of the first through third examples, the edge of the region of interest is a distance away from the position of the user cursor smaller than the radius of the geodesic propagation.

As used herein, an element or step recited in the singular and preceded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   obtaining three-dimensional (3D) multi-volume imaging data, the 3D multi-volume imaging data comprising a plurality of registered image volumes;
   determining one or more positions of a user cursor within a first image of a first image volume of the plurality of registered image volumes;
   determining a contour point position corresponding to each of the one or more positions of the user cursor for two or more of the plurality of registered image volumes;
   generating two or more segmentation contours corresponding to the two or more of the plurality of registered image volumes based on the contour point position for each of the one or more positions of the user cursor, wherein generating each of the two or more segmentation contours comprises, for each of the one or more positions of the user cursor, defining a geodesic propagation around a position of the user cursor, wherein the geodesic propagation is a circle and a radius of the geodesic propagation depends on tonal distributions within the geodesic propagation;
   determining, via user input to a display device, a selected segmentation contour of the two or more segmentation contours;

generating a three-dimensional (3D) segmentation mask based at least in part on the selected segmentation contour; and saving the 3D segmentation mask to memory.

2. The method of claim 1, wherein the plurality of registered image volumes are each partitioned into a plurality of image slices and the first image is a first image slice of the first image volume.

3. The method of claim 1, wherein a contour point to which the contour point position corresponds is one of a plurality of points of a corresponding segmentation contour.

4. The method of claim 1, wherein the 3D multi-volume imaging data is acquired by an imaging system configured to acquire one of multi-parametric and multi-phase imaging data.

5. The method of claim 1, wherein a representation of the segmentation mask is displayed to the user via the display device.

6. The method of claim 1, wherein each of the plurality of registered image volumes includes data of a region of interest and the segmentation mask corresponds to the region of interest.

7. The method of claim 1, wherein the position of the user cursor is within a distance of a region of interest of the first image, the distance being less than a radius of the geodesic propagation, and wherein generating each of the two or more segmentation contours comprises, for each of the one or more positions of the user cursor:

detecting one or more gradients within the geodesic propagation, wherein the one or more gradients correlate to an edge of the region of interest;

defining the edge of the region of interest based on the one or more gradients; and determining a point of the edge that is closest to the position of the user cursor, wherein the point is one of two or more points of a corresponding segmentation contour.

8. The method of claim 1, wherein generating the segmentation mask comprises interpolating between two or more selected segmentation contours.

9. A system, comprising:

an imaging system configured to acquire three-dimensional (3D) multi-volume imaging data; and a computing device communicably coupled to the imaging system, the computing device configured with instructions stored in non-transitory memory executable by a processor that, when executed, cause the processor to:

obtain a 3D multi-volume imaging dataset from an imaging archive, wherein the 3D multi-volume imaging dataset comprises a plurality of registered image volumes each comprising a plurality of image slices;

display an image slice of a first set of image slices of two or more image volumes of the plurality of registered image volumes within a graphical user interface (GUI) of a display device communicably coupled to the computing device;

determine two or more positions of a user cursor within a first image slice of a first image volume in response to user input;

determine contour points within two or more image slices corresponding to two or more of the plurality of registered image volumes based on the two or more positions of the user cursor within the first image slice, wherein positions of the contour points are further determined based on one or more gradients in pixel intensity detected within a geodesic propagation around the two or more positions of the user cursor, wherein the one or more gradients in pixel intensity are correlated with one or more edges of a region of interest (ROI) and the one or more edges are defined based on the one or more gradients in pixel intensity;

generate two or more segmentation contours, wherein each of the two or more segmentation contours corresponds to one of the two or more image slices and comprise respective pluralities of contour points and the two or more segmentation contours are generated based on determining a closest point of the one or more edges to each given contour point;

select, in response to user input, a selected segmentation contour of the two or more segmentation contours;

generate, based on the selected contour, a 3D segmentation mask; and save the 3D segmentation mask to non-transitory memory.

10. The system of claim 9, wherein each of the plurality of registered image volumes corresponds to one of a different imaging sequence and a different imaging phase.

11. The system of claim 9, wherein each of the two or more segmentation contours is displayed on the display device with a different color, wherein a first segmentation color is displayed with a first color and a second segmentation contour is displayed with a second, different color.

12. The system of claim 9, wherein two or more positions of the user cursor are known within each of the two or more image slices.

13. The system of claim 9, wherein the computing device is further configured with instructions stored in non-transitory memory that when executed, cause the processor to determine two or more second segmentation contours corresponding to a second set of image slices.

14. The system of claim 13, wherein the computing device is further configured with instructions stored in non-transitory memory that when executed, cause the processor to select, in response to user input, a second selected segmentation contour of the two or more second segmentation contours.

15. A method, comprising:

determining a position of a user cursor within a first image of a first image volume of a plurality of image volumes of a 3D multi-volume imaging dataset;

generating a geodesic propagation around the position of the user cursor within two or more images of two or more corresponding image volumes of the plurality of image volumes;

determining pixel intensities within the geodesic propagation of each of the two or more images;

defining an area that approximates an edge of a region of interest within the geodesic propagation of each of the two or more images based on one or more gradients in pixel intensity, wherein when the one or more gradients in pixel intensity are detected within the geodesic propagation based on the determined pixel intensities, the area is not a circle and when one or more gradients in pixel intensity are not detected within the geodesic propagation based on the determined pixel intensities, the area is a circle;

determining a point of the edge closest to the position of the user cursor within each of the two or more images; and saving the point as one of a plurality of points of a segmentation contour for each of the two or more images.

16. The method of claim 15, further comprising generating a segmentation mask based at least in part on a selected segmentation contour of one of the two or more images and displaying a representation of the segmentation mask.

17. The method of claim 15, wherein a prior point of a respective segmentation contour stabilizes the point.

18. The method of claim 15, wherein the geodesic propagation is constrained to a radius depending on tonal distributions within the geodesic propagation.

19. The method of claim 18, wherein the edge of the region of interest is a distance away from the position of the user cursor smaller than the radius of the geodesic propagation.

* * * * *